United States Patent
Yayon

(10) Patent No.: US 7,887,831 B2
(45) Date of Patent: Feb. 15, 2011

(54) BONE ENHANCING COMPOSITE

(75) Inventor: Avner Yayon, Moshav Sitria (IL)

(73) Assignee: Hepacore Ltd., Ness Ziona (IL)

( * ) Notice: Subject to any disclaimer, the term of this patent is extended or adjusted under 35 U.S.C. 154(b) by 1466 days.

(21) Appl. No.: 10/534,794

(22) PCT Filed: Nov. 13, 2003

(86) PCT No.: PCT/IL03/00962

§ 371 (c)(1),
(2), (4) Date: Nov. 7, 2005

(87) PCT Pub. No.: WO2004/043333

PCT Pub. Date: May 27, 2004

(65) Prior Publication Data

US 2006/0147547 A1    Jul. 6, 2006

(30) Foreign Application Priority Data

Dec. 26, 2002    (IL) .................................... 153699

(51) Int. Cl.
*A61F 2/28* (2006.01)
(52) U.S. Cl. ................................................ 424/426
(58) Field of Classification Search .................. None
See application file for complete search history.

(56) References Cited

U.S. PATENT DOCUMENTS

| | | | |
|---|---|---|---|
| 4,880,610 A | 11/1989 | Constantz | 423/309 |
| 5,071,436 A | 12/1991 | Huc | 424/423 |
| 5,227,147 A * | 7/1993 | Yoshimura et al. | 423/308 |
| 5,281,265 A | 1/1994 | Liu | 106/35 |
| 5,650,176 A | 7/1997 | Lee | 424/602 |
| 5,676,976 A | 10/1997 | Lee | 424/602 |
| 5,683,461 A | 11/1997 | Lee | 424/423 |
| 5,733,564 A | 3/1998 | Lehtinen | 424/423 |
| 5,770,229 A | 6/1998 | Tanihara | 424/488 |
| 6,027,742 A | 2/2000 | Lee | 424/422 |
| 6,118,043 A | 9/2000 | Nies | 623/23.56 |
| 6,214,368 B1 | 4/2001 | Lee | 424/423 |
| 6,231,607 B1 | 5/2001 | Ben-Bassat | 623/16.11 |
| 6,331,312 B1 | 12/2001 | Lee | 424/426 |
| 6,375,935 B1 | 4/2002 | Constantz | 424/57 |
| 6,417,247 B1 | 7/2002 | Armstrong | 523/115 |
| 7,507,286 B2 * | 3/2009 | Edidin et al. | 106/690 |

FOREIGN PATENT DOCUMENTS

| | | |
|---|---|---|
| EP | 1208850 A1 | 5/2002 |
| WO | WO 00/47214 | 8/2000 |

OTHER PUBLICATIONS

Pollik, S., et al., J Oral Maxillofac Surg, 53(8):915-22; 1995.
Rabie, et al., Int J Oral Maxillofac Surg 25(5):383, 1996.
Schwarz et al., J Orthop Res, 18:849-55, 2000.
Taylor et al., Int J Oral Maxillofac Implants, 17:321-30, 2002.

(Continued)

*Primary Examiner*—Carlos A Azpuru
(74) *Attorney, Agent, or Firm*—Heslin Rothenberg Farley & Mesiti P.C.

(57) ABSTRACT

A bone-enhancing composite material comprising synthetic apatite and at least one supplementary bioactive agent selected from a biocompatible polymer and an anti-resorptive agent added ab initio, methods of preparing said composite and uses thereof are provided. The physical and biological properties of the composite are controlled by the addition of specific supplementary bioactive agents as well as optional therapeutic agents. The composite may be used as a powder, a paste or an implant.

32 Claims, 18 Drawing Sheets

OTHER PUBLICATIONS

Hunziker, Osteoart. Cart., 10:432-465, 2002.
LeGeros, Clin Orthop 395:81-98, 2002.
Denissen, et al. Bone Miner. 25:123-134, 1994.
Ben-Bassat et al, in Biomaterials Engineering and Devices: Human Applications v2, p. 155-169, 2000.
Cancer Treat Rev 28(6):305-19, 2002.
Bolander, Proc. Soc. Exp. Biol. Med. 200(2): 165, 1992.
Barralet, J. et al., J Biomed Mater Res 49(2):176-82, 2000.
Chole, R., et al. Jaro 2:65-71, 2001.
Colombier et al., Cells Tissues Organs 164:131-140,1999.
Denissen, et al, J Periodontol, 71:279-86, 2000.
Fujibayashi et al., J Long Term Eff Med Implants; 11:93-103, 2001.
Hollinger (Hollinger and Kleinschmidt, J Craniofacial Surg 1:60-68, 1990.

* cited by examiner

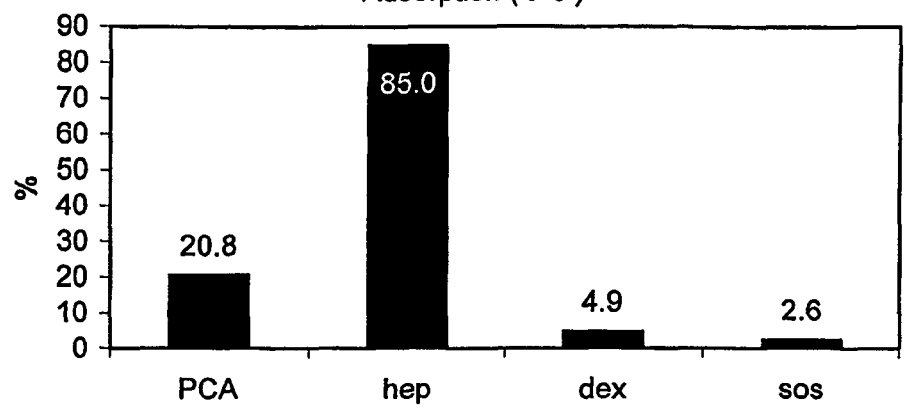
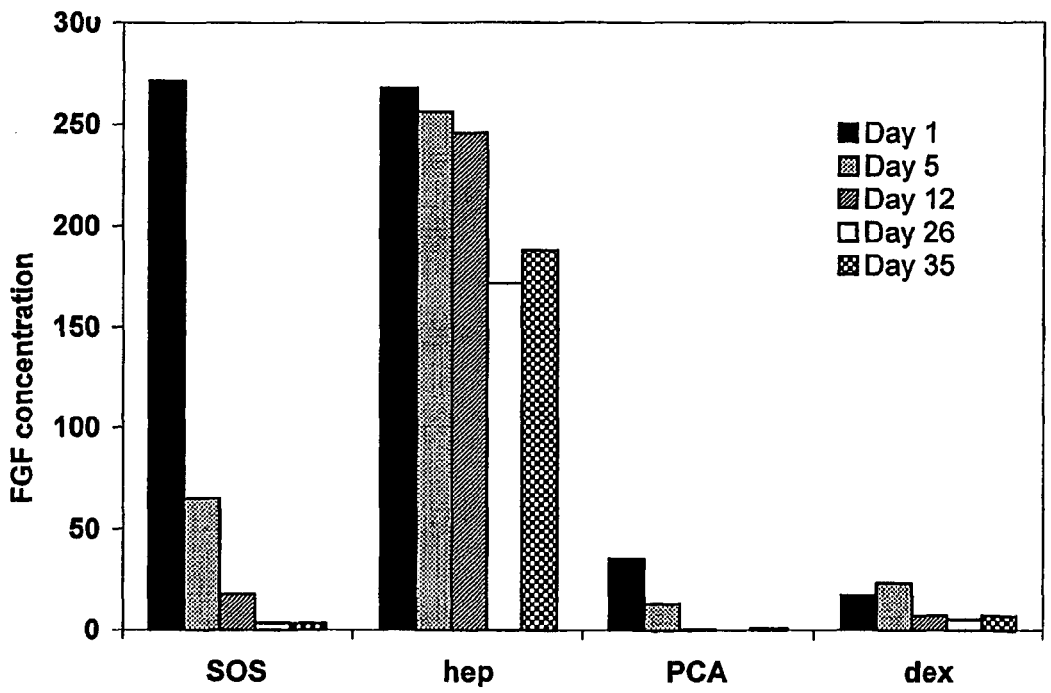

BONE ENHANCING COMPOSITE

CROSS REFERENCE TO RELATED APPLICATIONS

This application is a 371 filing of PCT International Application No. PCT/M2003/000962 filed Nov. 13, 2003 and published in English as WO 2004/043333 on May 27, 2004, which claims the priority of PCT Application No. PCT/TL02/00913 filed Nov. 14, 2002 and of Israeli Application No. 153699 filed Dec. 26, 2002, the disclosures of which are hereby incorporated by reference in their entirety.

FIELD OF THE INVENTION

The present invention relates to the field of tissue engineering and more specifically to a bone-enhancing composite comprising synthetic apatite and at least one supplementary bioactive agent selected from a biocompatible polymer and an anti-resorptive agent introduced into the composite ab initio suitable for use as a bone graft implant, a method of preparing the composite and uses thereof.

BACKGROUND OF THE INVENTION

Tissue engineering may be defined as the art of reconstructing mammalian tissues, both structurally and functionally (Hunziker, Osteoart. Cart., 10:432-465, 2002). In general, tissue engineering includes the delivery of a polymeric or ceramic scaffold that serves as an architectural support onto which cells may attach, proliferate, and synthesize new tissue to replace tissue losses due to disease, trauma or age. Innovations in orthopedic surgery include a vast array of biomaterials that provide mechanical stability, controlled release of therapeutic agents and a scaffold for cell anchorage.

Bone

Bone is a unique type of tissue made up of an inorganic mineral phase and cellular and extracellular matrix phases. Bone is a vital organ that undergoes modeling and remodeling wherein old bone is lost (resorption) and new bone is formed (formation/replacement). Although bone has an inherent capacity for repair and regeneration when damaged by disease or trauma, the renewed bone is often fragile and not weight bearing. Bone restoration or replacement is a viable consideration in indications including osteopenia, osteoporosis, bone tumors, spinal fusion, fractures and non-union fractures.

Bone formation may be enhanced either by recruiting osteoblasts, the bone forming cells, or by inhibiting recruitment or activity of osteoclasts, the bone resorbing cells. Osteoblasts and osteoclasts work together in a coordinated fashion to form and remodel bone tissue.

Many materials have been suggested for bone repair, specifically materials that avoid the harvesting problems associated with autologous matter and the health risks associated with allogenic material. Inorganic material such as calcium phosphate has been utilized as bone and dental fillers (reviewed in LeGeros, Clin Orthop 395:81-98, 2002). Apatite, a particulate calcium phosphate, is particularly appealing by virtue of the fact that it is the naturally occurring mineral component in bone and teeth. Bone apatite exhibits low crystallinity due to the presence of magnesium and carbonate ($CO_3$) ions. Lack of crystallinity in apatites is associated with increased solubility in vivo. Hydroxyapatite, in contrast, exhibits high crystallinity and represents a small component of natural bone. Synthetic bone substitute materials comprising calcium phosphate or hydroxyapatite have been disclosed for use as bone grafts implants and cements.

U.S. Pat. No. 4,880,610 teaches a method for producing an injectable calcium phosphate mineral bone-like material using highly concentrated phosphoric acid, a calcium source and a neutralizing source, to which various additives may be incorporated, including sugars or proteins such as collagen, fibrinogen or elastin.

U.S. Pat. Nos. 5,650,176; 5,676,976 and 5,683,461 teach the synthesis of reactive amorphous calcium phosphates (ACP) and their use for promoting bone growth. U.S. Pat. No. 6,214,368 discloses an injectable bone substitute comprising the reactive ACP, an acidic second calcium phosphate material and liquid to form an injectable paste capable of hardening in vivo.

U.S. Pat. No. 5,281,265 discloses surgical cement comprising a calcium-based cementing component and a setting component capable of hardening in vivo. U.S. Pat. No. 6,375,935 discloses a flowable calcium phosphate composition that hardens in vivo.

U.S. Pat. No. 5,071,436 discloses a spongy bone substitute matrix consisting of glycosaminoglycans bonded to collagen together with hydroxyapatite. U.S. Pat. No. 6,118,043 discloses a porous bone replacement material consisting essentially of calcium minerals having an FGF polypeptide contained within.

U.S. Pat. Nos. 6,027,742 and 6,331,312 disclose a bioceramic composite capable of resorption in the body. The composition comprises resorbable poorly crystalline apatite (PCA) as a cement formed from amorphous calcium phosphate, a promoter and a biocompatible supplementary material selected from bioresorbable polymers or non-resorbable material, which impart a desirable biological, chemical or mechanical property. The composite is prepared by combining the PCA with the supplementary material.

U.S. Pat. No. 6,417,247 provides a composition comprising a polymer or polymer solution that forms a gel under controlled parameters and a ceramic matrix, the composition being fluid under non-physiological conditions and non fluid under physiological conditions. The compositions are prepared by mixing the ceramic component into a polymer solution.

EP 1208850A1 discloses a bone repair paste comprising an osteogenic promoter, a calcium component and a viscosity-increasing agent. The paste is prepared by admixing the three components to yield a sustained-release paste.

U.S. Pat. No. 6,231,607 discloses a novel bone substitute comprising hydroxy apatite and both α- and β-tricalcium phosphate (TCP), prepared by microwave irradiation and subsequent sintering. The intermediate powder material, resulting from microwave radiation, exhibits strong similarity to natural bone according to X-ray diffraction (XRD) and Fourier transform infrared (FTIR) spectroscopy analyses. Derivatives or a fluid composition comprising the dry powder were neither taught nor suggested in that disclosure.

Anti-Resorptive Agents

Anti-resorptive agents such as bisphosphonates have been widely used to prevent bone resorption and lower fracture risk in patients with osteoporosis and other diseases exhibiting osteolytic processes. Certain bone implants and cements comprising an anti-resorptive agent have been disclosed for filling bone voids and bonding prosthetic devices to bone. Denissen et al (Bone Miner. 25:123-134, 1994) describe the use of bisphosphonate-impregnated ceramic hydroxyapatite implants for the maintenance of bone mass following tooth extraction due to oral disease.

U.S. Pat. No. 5,733,564 teaches a method of treating endoosteal materials by immersion in a bisphosphonate solution to enhance biocompatibility of prostheses. WO 00/47214 discloses anti-resorptive bone cements, comprising one or more anti-resorptive agents, preferably a bisphosphonate, useful for filling bone voids, bonding prosthetic devices to bone and for reconstructive bone surgery.

Existing bone graft implants, including pastes and cements, are prepared by admixing preformed calcium-based materials with a supplementary component such as a polymer or an anti-resorptive agent. In general, the calcium-based materials in the art, including synthetic apatites, are prepared using harsh conditions, e.g. low pH (phosphoric acid) or very high temperatures (>450° C.), thus precluding the generation of a composite incorporating such agents during the preparation steps. The art has not heretofore provided synthetic apatite composite material wherein a supplementary bioactive agent is included ab initio.

There remains an unmet medical need for a material having superior biological and physical properties for enhancing bone formation in orthopedic, periodontal and craniofacial indications.

SUMMARY OF THE INVENTION

Although numerous compositions comprising calcium phosphate minerals are known in the art, none has proven entirely satisfactory in meeting the criteria required for successful tissue engineering. The inventors of the present invention have found, quite surprisingly, that a novel composite material is produced by co-precipitating a liquid mixture of calcium, phosphate and carbonate ions with at least one amino acid molecule in monomeric or polymeric form and at least one supplementary bioactive agent selected from a biocompatible polymer and an anti-resorptive agent that is present in the mixture ab initio. The composite provides a superior material for orthopedic, periodontal and craniofacial applications where bone enhancement is desired. Bone enhancement may be accomplished either by recruiting osteoblasts, the bone forming cells or by inhibiting recruitment and activity of osteoclasts, the bone resorbing cells. The bone-enhancing composite may be used per se or as a carrier to deliver therapeutic agents to the site of the bone defect or lesion.

In one aspect the present invention provides a bone enhancing composite material comprising synthetic apatite and at least one supplementary bioactive agent selected from a biocompatible polymer and an anti-resorptive agent. Synthetic apatite is an artificial synthetic calcium phosphate material prepared by precipitating calcium and phosphate from a solution. In one embodiment the synthetic apatite comprises ionic calcium, phosphate and carbonate and at least one amino acid in monomeric or polymeric form. In another embodiment the synthetic apatite is poorly crystalline apatite (PCA), providing a bone replacement material superior to other synthetic apatite materials such as hydroxyapatite or β-tricalcium phosphate due to its similarity to natural bone and enhanced resorption capacity.

According to another aspect of the present invention, the at least one supplementary bioactive agent is introduced during the preparation step of the synthetic apatite ab initio. Without wishing to be bound by any theory, the presence of a biocompatible polymer and/or an anti-resorptive agent during the formation of the synthetic apatite generates a unique composite material wherein the supplementary bioactive agent is intercalated or dispersed or distributed within the poorly crystalline structure.

It is now disclosed that the attributes and desirable properties of the bone enhancing composite can be controlled by the addition of at least one supplementary bioactive agent selected from a biocompatible polymer and an anti-resorptive agent in the process of forming the synthetic apatite. The supplementary bioactive agent is selected from a group consisting of biocompatible polymers and anti-resorptive agents.

According to one aspect the at least on supplementary bioactive agent is biocompatible polymer. The composite comprising synthetic apatite and at least one biocompatible polymer has attributes that make it particularly advantageous for supporting and promoting bone growth and repair in vivo. Among the advantageous properties of the composite of the invention:

a) The composite has superior physical properties, controlled by various biocompatible polymers used in the preparation, including poor crystallinity that highly resembles that of natural bone, enhanced resorption and convenient formulation for use in vivo.

b) The composite has superior biological properties, controlled by various biocompatible polymers used in the preparation, including controlled release of therapeutic agents, biocompatibility, and the ability to promote cell growth, proliferation, differentiation and migration.

The at least one biocompatible polymer, which may be natural or synthetic, is selected to impart advantageous attributes to the composite. Without wishing to be bound by theory, the biocompatible polymers impart cohesive properties to the composite that may be optimized for each of the diverse applications.

According to one embodiment of the present invention the biocompatible polymers that impart the desired properties are natural polymers rather than synthetic polymers. Examples of natural biocompatible polymers include polysaccharides and oligosaccharides. According to one embodiment of the present invention the natural biocompatible polymer is a polysaccharide, preferably a sulfated polysaccharide such as a glycosaminoglycan selected from the group consisting of chondroitin 4-sulfate, chondroitin 6-sulfate, hyaluronic acid, dermatan sulfate, keratan sulfate, heparin, heparan sulfate, sucrose octasulfate, perlecan, syndecan, glypican and combinations thereof. Heparin is meant to include the multiple molecular weight derivatives of heparin including very low molecular weight heparin, low molecular weight heparin, heparan, and heparin mimetics. Hyaluronic acid is meant to include cross-linked and non-crosslinked hyaluronic acid materials. Additional natural biocompatible polymers include starch, collagen, gelatin, glycogen, chitin, cellulose, keratins or combinations thereof.

In one embodiment the bone enhancement composite comprises synthetic apatite and heparin or a derivative thereof.

According to another aspect the at least on supplementary bioactive agent is an anti-resorptive agent. The composite comprising synthetic apatite and at least one anti-resorptive agent has attributes that make it particularly advantageous for enhancing and preserving bone in vivo and for applications such as securing prosthetic devices to bone and filling lesions due to osteolytic processes such as metastases. Among the advantageous properties of the composite of the invention comprising the anti-resorptive agent:

a) The composite has superior physical properties, controlled by varying anti-resorptive agents used in the preparation, including crystallinity that resembles that of natural bone, retarded resorption, good mechanical stability, structural integrity and convenient formulation for use in vivo.

b) The composite has superior biological properties, controlled by varying anti-resorptive agents used in the preparation, including biocompatibility, local bone enhancement and increased bone mass and inhibition of osteolysis.

According to one embodiment of the invention the at least one anti-resorptive agent is a bisphosphonate or a pharmaceutically acceptable salt or ester thereof.

According to one aspect the present invention provides a composite comprising synthetic apatite, at least one supplementary bioactive agent selected from a biocompatible polymer and an anti-resorptive agent, further comprising at least one therapeutic agent selected from the group consisting of antibiotics, antiviral agents, chemotherapeutic agents, anti-rejection agents, analgesics and analgesic combinations, anti-inflammatory agents, hormones, growth factors and cytokines. According to another aspect the at least one therapeutic agent is a growth factor. According to one aspect the at least one therapeutic agent is selected from the group consisting of fibroblast growth factors (FGF) and bone morphogenetic proteins BMP), active fragments and variants thereof. Preferably a therapeutically effective amount of FGF is provided, said FGF having the capacity to induce bone growth and or angiogenesis.

These and other features result in a composite exhibiting advantageous properties including biocompatibility, biodegradability, osteoconductivity and osteoinductivity, controlled release of therapeutic agents and ease of administration.

The bone-enhancing composite comprising synthetic apatite and at least one supplementary agent selected from a biocompatible polymer and an anti-resorption agent is further characterized in that the composite has crystallinity similar to that of natural bone. In one aspect of the present invention the composite has an X-ray diffraction (XRD) pattern similar to that of poorly crystalline apatite and natural bone. In another aspect of the present invention the composite exhibits a peak of 2 theta (2θ) at about 26° and an undifferentiated peak of 2 theta (2θ) at about 31° to about 33°.

According to another aspect the composite comprises at least one bioactive polymer and at least one anti-resorptive agent.

According to one non-limiting embodiment the composite is prepared by microwave heating the calcium and phosphate ions with the supplementary agent using a procedure disclosed in U.S. Pat. No. 6,231,607. The powder resulting from that process consists of synthetic apatite or poorly crystalline apatite (PCA) calcium phosphate aggregates having a size of approximately 0.45 µm to about 6 µm in diameter, more preferably about 1 µm to about 4 µm in diameter. The aggregates are comprised of crystals of approximately 0.20 µm to about 0.50 µm in size.

In one aspect the bone enhancing composite exhibits a calcium to phosphate ratio (Ca/P) similar to that of natural bone. Accordingly, the synthetic apatite may contain cation or anion substitutions. In another aspect magnesium ions ($Mg^{++}$) and/or zinc ($Zn^{++}$) are added to partly replace the calcium ions, preferably $Mg^{++}$.

The bone-enhancing composite may be administered as a powder for certain bone disease and injury applications. In certain indications a fluid, semi-fluid or solid composition is preferred.

According to embodiment of the present invention a pharmaceutical composition comprising the bone-enhancing composite is provided. The composition may be fluid or semi-fluid. According to one embodiment of the present invention the composition is paste-like. According to another embodiment the composition is an injectable paste. According to yet another embodiment the viscosity of the injectable paste is in the range of about 10 to about 500 poises, more preferably in the range of about 30 to about 200 poises, depending on the application.

According to one embodiment of the present invention the pharmaceutical composition is fluid at temperatures below physiological conditions and non-fluid at physiological temperatures. Preferably the composition gels or hardens at about 35° C. to about 42° C. This particular property of the composition may be achieved by the addition of certain polymers or other additives to the composite of the invention.

In one aspect the composition comprises an additive that promotes in situ hardening of said composition within about 10 minutes to about 120 minutes following injection. A non-limiting example of such materials includes collagens such as a gel forming soluble collagen disclosed in WO 00/47130, and non-polymeric compounds such as a non-polymeric esters or mixed esters of one or more carboxylic acids disclosed in U.S. Pat. No. 6,413,536. Another non-limiting example includes the addition of calcium sulfate or calcium phosphate compounds. The composition may comprise about 5% to about 50% calcium sulfate.

Alternatively, in the reconstruction of structural tissues like cartilage and bone, certain applications may require the in vitro molding of the composition into three dimensional configuration articles of varying thickness and shape. Accordingly, provided is an implant comprising the composite of the invention further comprising a hardener, said implant having a specific shape including a sphere, screw, cube, rod, tube or plate.

In certain embodiments of the present invention a pharmaceutical composition is provided comprising a composite material wherein the composite material comprises synthetic apatite, at least one supplementary bioactive agent selected from a biocompatible polymer and an anti-resorptive agent, optionally further comprising at least one therapeutic agent, further comprising a pharmaceutically acceptable carrier or diluent. The pharmaceutical composition may optionally further comprise hardening agents, the hardening agents having the ability to induce setting of the composition into a solid article.

According to one embodiment of the present invention a pharmaceutical composition is provided comprising synthetic apatite and heparin composite, at least one carrier having sufficient fluidity to enable injection of the composition to the site of treatment. According to another embodiment of the present invention a pharmaceutical composition is provided comprising synthetic apatite and heparin composite, at least one carrier having sufficient fluidity to enable injection of the composition to the site of treatment and a therapeutically effective amount of at least one therapeutic agent selected from the group consisting of growth factors and their variants. According to yet another embodiment of the present invention the at least one therapeutic agent is selected from the group consisting of fibroblast growth factors (FGF) and bone morphogenetic proteins (BMP), active fragments and variants thereof. Preferably the growth factor has the capacity to induce bone growth and or angiogenesis.

The pharmaceutical composition of the present invention is useful for treating orthopedic, periodontal and craniofacial indications wherein there is need to fill a void in a bone, to secure a prosthetic device or a need to delivery therapeutic agents to the bone or tissue in contact with the bone. Tissue closely associated with bone includes, ligaments, tendons cartilage and muscle. In accordance with the invention use of the composite of the invention for the manufacture of a bone-enhancing medicament is provided. The medicament is useful for treating diseased or injured bone in orthopedic, periodontal and craniofacial indications wherein the medicament is provided alone or comprising therapeutic agents that accelerate the healing rate and enhance the quality of bone formation or treat a disease or traumatized bone associated tissue.

Further provided is a method of preparing the bone-enhancing composite. The method comprises the following steps:

a) preparing a liquid mixture comprising ionic calcium, phosphate, at least one amino acid in either monomeric or polymeric form, carbonate, at least one supplementary bioactive agent selected from a biocompatible polymer and an anti-resorptive agent, optionally further comprising a therapeutic agent;
b) subjecting said mixture to microwave irradiation;
c) quenching said irradiated mixture;
d) filtering said irradiated mixture so as to separate between the filtrate and a cake;
e) drying said cake;
f) grinding said dried cake into a powder;

According to one embodiment of the present invention the above process may further comprise the following steps:

g) sterilizing said powder;
h) wetting said sterilized powder with a solution optionally comprising at least one therapeutic agent;
i) preparing said wetted powder for administration.

According to one embodiment of the present invention step (g) is carried out in a manner that substantially retains the X-ray diffraction pattern of the powder, preferably by ionization techniques, more preferably by γ-irradiation. The present inventors have found that following sterilization by γ-irradiation the bone enhancing composite retains its molecular crystal structure, as determined by X-ray diffraction analysis. Preferably the composite retains an X-ray diffraction pattern having a peak of 2 theta at about 25° to about 26° and an undifferentiated peak of 2 theta at about 31° to about 33°. The bone-enhancing material may be sterilized by thermal sterilization, preferably at about 140° C. to about 160° C. for at least 30 minutes, and retain its XRD.

According to one embodiment of the present invention step (h) of the above method is performed using a pharmaceutically acceptable liquid such as water or a physiological fluid. The liquid is added in a sufficient amount to permit wetting and dispersion of the powder to form a wetted mixture having the consistency of a paste, cement or putty. The liquid may advantageously comprise at least one therapeutic agent selected from antibiotics, antiviral agents, anti-rejection agents, analgesics and analgesic combinations, anti-inflammatory agents, hormones, growth factors, cytokines and chemotherapeutic agents including anti-cancer compounds.

The therapeutic agents, for example, growth factors, angiogenic factors, and the like, are likely to encourage a more rapid growth of the cells within the implant, or a more rapid vascularization of the implant Such factors may be too small to be effectively retained within the matrix and hence are introduced in the form of slow-release or controlled-release formulations into the matrix to provide for their effectiveness.

In yet another embodiment a method for treating orthopedic, periodontal and craniofacial indications comprising administering to a subject in need thereof a therapeutically effective amount of a composition comprising synthetic apatite, at least one biocompatible polymer, optionally further comprising at least one therapeutic agent.

Further provided is the use of a composite comprising synthetic apatite and at least one supplementary bioactive agent selected from a biocompatible polymer and an anti-resorptive agent, optionally further comprising a therapeutic agent for the preparation of a medicament for the treatment of orthopedic, periodontal and craniofacial indications.

Depending on the indication the bone-enhancing composite may be used per se or in a wetted form. According to one embodiment the bone substitute is a powder and is used per se. According to one embodiment the paste-like material is administered directly to a bone defect. According to one currently more preferred embodiment the paste-like material is inserted into a syringe for local administration. According to one embodiment the paste-like material hardens in situ in about 10 minutes to about 120 minutes following injection. Alternatively, the paste-like material hardens in vitro to form a molded implant.

Furthermore, the composite may be used as a coating on synthetic or other implants such as pins and plates, for example, in hip replacement procedures. Thus, the present invention further provides implants or medical devices coated with the matrix of the invention. In a non-limiting example the bone enhancing composite comprising synthetic apatite and at least one anti-resorptive agent may be used to reduce the incidence of osteolytic debris induced by the wear and corrosion of orthopedic prostheses.

Yet another currently preferred embodiment of the present invention provides a kit comprising the disclosed bone graft composition, where the dry and liquid components may be present in separate containers in the kit, or some of the components may be combined within one container.

These and other aspects of the present invention will be apparent from the description, figures and claims that follow.

BRIEF DESCRIPTION OF THE FIGURES

FIG. 2 shows the particles of the bone-enhancing composites as seen in SEM (scanning electron microscope).

FIG. 3A shows the results of the adsorption assay and FIG. 3B shows the results of the proliferation assay for FGF on synthetic apatite, per se or composite. Proliferation was tested on FGFR1 expressing FDCP cells.

FIG. 6A shows bone formation in an untreated hole, FIG. 6B shows new bone surrounding a commercially available calcium phosphate ceramic. FIG. 6C shows the new bone surrounding the synthetic apatite particles while FIG. 6D shows new bone surrounding synthetic apatite-heparin composite particles. FIG. 6D shows full integration between new bone and the implanted particles.

DETAILED DESCRIPTION OF THE INVENTION

Figure 1A:
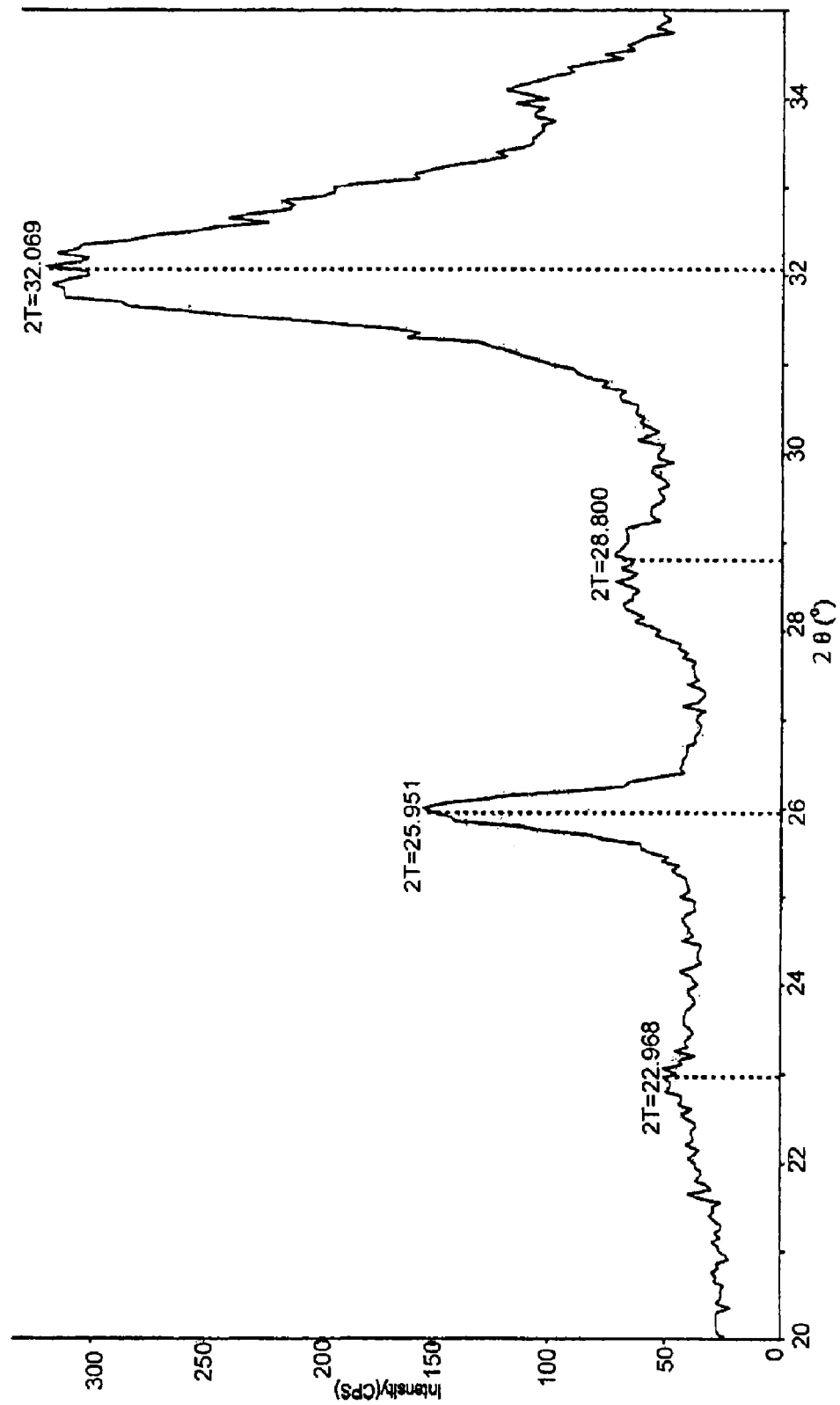
FIGS. 1A-1H show the X-Ray diffraction patterns of the bone enhancing composites comprising synthetic apatite and a biocompatible polymer or synthetic apatite and an anti-resorptive agent.

The present invention is directed to a biocompatible composite comprising synthetic apatite and at least one supplementary bioactive agent selected from a biocompatible polymer and an anti-resorptive agent useful as a bone enhancing implant.

In principle, an ideal bone enhancing material will exhibit the following properties:
Biocompatible: minimal toxicity and maximal resemblance to natural bone.
Practical: convenient for use by the medical practitioner.
Resorbable: capacity to biodegrade in the host over time.
Osteoinductive: capacity to induce regeneration or enhancement of functional bone.

In addition, the bone enhancing material may also exhibit the following properties:
Osteoconductive: provide a microenvironment beneficial to attachment, migration and proliferation of cellular elements involved in bone growth.

The present invention provides a bone-enhancing composite exhibiting the aforementioned advantageous properties.

Bone enhancement may be accomplished either by recruiting osteoblasts, the bone forming cells or by inhibiting recruitment or activity of osteoclasts, the bone resorbing cells. Accordingly, a bone-enhancing material may stimulate de novo bone formation or may inhibit bone resorption.

Definitions

For convenience and clarity certain terms employed in the specification, examples and claims are described herein.

The term "synthetic apatite" refers to an artificial synthetic calcium phosphate material prepared by precipitating calcium and phosphate from a solution. Synthetic apatite may further comprise other materials including carbonate ions, and magnesium or zinc.

"Poorly crystalline apatite" and "PCA", refer to synthetic poorly crystalline apatitic calcium phosphate. PCA has substantially the same X-ray diffraction spectrum as natural bone. The spectrum is generally characterized by two peaks in the region of 2 theta $2\theta$ at 25°-35°, with one centered at about 25° to about 26° and the other centered at about 32°.

The term "biocompatible" as used herein refers to materials having affinity with living tissues, low toxicity and no unacceptable foreign body reactions in the living body. In one aspect "biocompatible polymer" refers to a biodegradable polymer.

The term "osteoconductive" as used herein refers to materials that provide a microenvironment that is advantageous to the healing of diseased or damaged bone. Preferably, the composite of the invention provides a milieu that is advantageous to the infiltration and proliferation of cells involved in the process of bone repair.

A "composite" as used herein refers to a material that is made up of two or more distinct elements. The composite of the invention is unique in that it comprises a mineral phase and an organic phase that are intercalated or interdispersed ab initio.

A composite or composition considered "resorbable" is soluble and degrades in vivo. Preferably, the material remains intact throughout the initial healing of the bone and degrades slowly as the host's cells invade and proliferate within the area of the implant. "Biodegradable" refers to the resorption of the composite or composition within the host in a manner that is non-toxic and non-immunogenic to the host.

The term "fluid" as used herein is intended to describe a composition having sufficient viscosity so as not to disperse from the space it is intended to fill, yet having a viscosity low enough to be able to be administered via syringe.

The term "viscosity" refers to the property of resistance to flow in a fluid or semi-fluid. Viscosity is measured in a unit known as a poise. Suitable viscosities of the final solution mixture of the pharmaceutical composition for each particular application may readily be established by the skilled person, but will generally be in the range of about 10 to about 500 poises, preferably about 30 to about 200 poises.

This term "implantation" refers to the insertion of the composition of the invention into a patient, whereby the implant serves to replace, fully or partially, tissue that has been damaged or removed. Another aspect of implantation is also taken to mean the use of the composite as a vehicle to transport therapeutic agents to a certain site in a patient. In this aspect there is also included the adsorption onto the composite or of a therapeutic agent selected from growth factors, cytokines, chemotherapeutic drugs, enzymes, anti-microbials, anti-inflammatory agents. A fluid, semi-fluid or solid material may be implanted.

The term "injection" refers to the insertion of a composition of the invention into a mammal using a syringe or other device which allows administration of the composition directly to the site of treatment. Another aspect of injection is also taken to mean the use of the composite as a vehicle to transport therapeutic drugs and therapeutic agents to a certain site in a patient. In this aspect there is also included the introduction into the composite of a therapeutic agent selected from growth factors, cytokines, enzymes, anti-microbials, anti-inflammatory agents and chemotherapeutic agents such as anti-cancer drugs.

Therapeutic agents including growth factors, angiogenic factors, and the like, are advantageous to encourage a more rapid growth of the cells within the composite, or a more rapid vascularization of the material thus reducing the healing time. Such factors may be too small to be effectively retained within the composition and hence may be introduced in the form of slow-release or controlled-release formulations into the composite to provide for their effectiveness.

Chemotherapeutic agents include a variety of chemical compounds that prevent or treat tumors and their metastases.

The inventors of the present invention have found that a novel composite material is produced by co-precipitating a liquid mixture of calcium, phosphate and carbonate ions with at least one amino acid molecule in monomeric or polymeric form and at least one supplementary bioactive agent selected from a biocompatible polymer and an anti-resorptive agent that is present in the mixture ab initio.

Biocompatible Polymers

According to one embodiment of the present invention the composite comprises at least one biocompatible polymeric agent that modulates the physical and biological properties including crystallinity, surface adhesion, cohesion, ability to maintain cell growth and proliferation, and binding and retention of therapeutic agents for controlled release.

These biocompatible polymers include materials belonging to the family of polysaccharides, anionic polysaccharides, glycosaminoglycans, or synthetic biocompatible polymers, including hyaluronic acid, pectin, alginate, galactans, galactomannans, glucomannans, polyuronic acids, heparin, dextran sulfate, dermatan sulfate, heparin, heparan sulfate, keratan sulfate, hexuronyl hexosaminoglycan sulfate, chondroitin 4-sulfate, chondroitin 6-sulfate, dermatan sulfate, keratan sulfate, perlecan, syndecan, glypican and PEG and combinations thereof According to one embodiment, the composite is prepared using a biocompatible polymer wherein the biocompatible polymer is heparin or a heparin derivative or heparin mimetic. "Heparin mimetic" as used herein includes polysulfated sugars, such as polysulfated monosaccharides, polysulfated disaccharides and polysulfated oligosaccharides, including sucrose octasulfate, inositol hexasulfate, and many other polysulfated sugars that may act as analogs of low molecular weight heparins may be used to substitute for sulfated polysaccharides. For example, U.S. Pat. No. 6,143,730 discloses sulfated oligosaccharides comprising from 3 to 8 monosaccharide units.

An "anionic polysaccharide" as used herein, is a polysaccharide, including non-modified as well as chemical derivatives thereof, that contains at least one negatively charged group (e.g., sulfate groups which are negative at neutral pH, and carboxyl groups at pH values above about 4.0) and includes salts thereof, such as sodium or potassium salts, alkaline earth metal salts such as calcium or magnesium salts. Non-limiting examples of anionic polysaccharides include pectin, alginate, galactans, galactomannans, glucomannans and polyuronic acids.

Anti-resorptive Agents

According to one embodiment the present invention is directed to a composite comprising synthetic apatite and at least one supplementary bioactive agent wherein the supplementary bioactive agent is an anti-resorptive agent. The composite is useful as an implant for treating bone disorders and diseases or as cement to anchor prostheses in certain orthopedic and dental indications.

The term "resorption" or "bone resorption" refers to the normal process of bone erosion by a group of cells known as osteoclasts. In remodeling, the bone building cells, osteoblasts, infiltrate and fill the resorption sites to form functional bone. Normally, bone resorption equals bone formation. However, in certain diseases and disorders bone resorption surpasses bone formation and bone loss occurs, increasing an individuals risk for osteoporosis and related bone-weakening diseases.

The term "anti-resorptive agent" as used herein refers to a compound, or drug having the ability to prevent, delay or reduce resorption of bone or of an implant. Examples of anti-resorptive agents include phosphonates, preferably bisphosphonates and derivatives thereof. Other anti-resorptive agents include estrogens, prostaglandins and calcitonin.

The terms "bisphosphonate" or "bisphosphonic acid" as used herein, relate to those phosphonates or phosphonic acids that have two phosphonate groups attached to the same carbon atom. Based upon their chemical composition bisphosphonates can be classified into nitrogen containing, N-bisphosphonates, including alendronate, zolendronate and pamidronate and non-nitrogen containing bisphosphonates including clodronate and etidronate. Bisphosphonates are potent inhibitors of bone resorption and are effective in treating diseases and disorders of bone resorption. Many bisphosphonates are known in the art, exhibiting different anti-resorptive potency that can be exploited in the preparation of the composite. For example, risedronate and zolendronate (contain a nitrogen atom in heterocyclic side group) are more potent than etidronate in inhibiting bone erosion. It is to be understood that the bisphosphonates useful herein include as non-limiting examples, e.g., alendronate, clodronate (clodrinate), etidronate, pamidronate, medronate, nedrinate, tiludronate, zolendronate or combinations thereof. Other non-limiting examples of bisphosphonates have been disclosed in U.S. Pat. Nos. 5,856,314 and 5,338,731.

Furthermore certain bisphosphonate compounds have anti-tumor activity per se (reviewed in Cancer Treat Rev 28(6): 305-19, 2002). This feature renders them useful for the treatment of bone metastases in certain cancers. The term "osteolysis" refers to the dissolution of bone.

According to one embodiment the present invention provides a composite comprising synthetic apatite and at least one anti-resorptive agent. According to another embodiment the at least one anti-resorptive agent is a bisphosphonate or bisphosphonate derivative or salt or ester thereof. According to yet another embodiment the present invention provides a composite comprising synthetic apatite and at least one anti-resorptive agent wherein the synthetic apatite is a poorly crystalline apatite and the at least one anti-resorptive agent is a bisphosphonate or bisphosphonate derivative or salt or ester thereof.

In certain circumstances local administration of bisphosphonate is preferred over systemic delivery. Non-limiting examples include maintaining integrity of a prosthesis and treating or preventing periprosthetic bone resorption. Another exemplary indication is to prevent local bone loss due to absence of weight bearing resulting from injury or trauma. Systemic administration of bisphosphonates to patients having bone loss due to the absence of weight bearing resulting from a bone injury is well known in the art Patients with renal disease, digestive disorders and other indications may not be candidates for systemic delivery of bisphosphonates and would benefit from local delivery.

Therapeutic Agents

According to one embodiment the present invention provides a composite comprising synthetic apatite and at least one supplementary bioactive agent selected from a biocompatible polymer and an anti-resorptive agent further comprising at least one therapeutic agent including drugs such as antibiotics and antiviral agents; chemotherapeutic agents; anti-rejection agents; analgesics and analgesic combinations; anti-inflammatory agents; hormones such as steroids and growth factors such as fibroblast growth factor. Further provided by the present invention is a composition comprising the composite impregnated with a drug or agent able to deliver high tissue levels of said drug to the site of injured or diseased bone or to a tissue associated with bone. A composite of this type is particularly useful for, but not limited to, delivering antibiotic therapy to osteomyelitis patients.

According to another embodiment of the present invention, the at least one therapeutic agent include cytokines, growth factors and their activators etc. for example, in order to enhance a therapeutic effect or to provide a slow-release or sustained-release mechanism. For example, growth factors, structural proteins or cytokines which enhance the temporal sequence of bone repair, alter the rate of proliferation or increase the metabolic synthesis of extracellular matrix proteins are useful additives to the composite of the present invention. Representative proteins include bone growth factors (BMPs, IGF) including BMP2 and BMP7 and fibroblast growth factors, including FGF2, FGF4, FGF9 and FGF18 and variants thereof for bone and cartilage healing. Other factors shown to act on cells forming bone include retinoids, growth hormone (GH), leptin and transferrin. Other therapeutic agents intended to be incorporated in the present invention include blood factors that regulate clot formation such as fibrin and plasminogen.

The proteins of the invention are polypeptides or derivatives, muteins or variants thereof, obtained from natural, synthetic or recombinant sources, which exhibit the ability to stimulate DNA synthesis and cell division in vitro of a variety of cells, particularly cell types involved in bone regeneration and remodeling. A non-limiting example of FGF variants is disclosed in WO 02/36732.

Additionally, cells genetically engineered to express the aforementioned proteins are including in the present invention. Preferred examples for bone repair uses periosteal or other mesenchymal stem cells or osteocytes/osteoblasts per se or transfected with bone growth factor genes selected from a group including bone morphogenetic protein (BMP) family genes or fibroblast growth factor (FGF) family genes. According to one currently preferred embodiment of the present invention the composite comprises at least one growth factor of the FGF family having osteoinductive activity. According to one currently more preferred embodiment of the present invention the composite further comprises a growth factor of the BMP family.

According to one embodiment the composite comprising synthetic apatite and at least one anti-resorptive agent further comprise at least one therapeutic agent selected from antibiotics and antiviral agents; chemotherapeutic agents; anti-rejection agents; analgesics and analgesic combinations; anti-inflammatory agents or hormones such as steroids.

The mineral component of bone is predominantly made of calcium phosphate. "Hydroxy apatite" refers to a highly crystalline calcium phosphate having the chemical formula: $Ca_5(PO_4)_3OH$. Hydroxy apatite and other highly crystalline synthetic apatite materials are considered to be less than optimal bone substitute implants since, although they are biocompatible, they are for the most poorly biodegradable. The mineral fraction of natural bone is primarily composed of "poorly crystalline apatite", a calcium phosphate derivative. It is to be understood that a portion of the calcium ($Ca^{++}$) ions may be replaced with other divalent ions selected from the group consisting of Magnesium ($Mg^{++}$) and Zinc ($Zn^{++}$). The incorporation of additional or different divalent ions imparts on the composition certain properties that may be advantageous to bone repair and growth.

Matrix Preparation

According to one embodiment the present invention provides a pharmaceutical composition comprising synthetic apatite and at least one supplementary bioactive agent selected from a biocompatible polymer and an anti-resorptive agent further comprising a pharmaceutically acceptable carrier or excipient. According to one embodiment of the present invention the pharmaceutical composition further comprises at least one therapeutic agent.

According to one embodiment of the present invention a pharmaceutical composition comprising synthetic apatite and heparin composite, at least one carrier having sufficient fluidity to enable injection of the composition to the site of treatment and at least one therapeutic agent selected from the group consisting of growth factors and their variants is provided. According to one currently most preferred embodiment of the present invention the at least one therapeutic agent is selected from the group consisting of fibroblast growth factors and their variants.

The pharmaceutical composition of the present invention is useful for treating orthopedic, periodontal and craniofacial indications wherein there is need to fill a void in a bone including fractures, non-union fractures, spinal fusion and other indications. According to certain embodiments the pharmaceutical composition is useful for the delivery of therapeutic agents to a bone lesion or defect. According to other embodiments, the pharmaceutical composition of the present invention is useful for cementing prostheses or to prevent osteolysis. The pharmaceutical composition of this invention may be administered as a paste, preferably as an injectable paste, more preferably as an injectable paste that hardens in situ, within 24 hours following implantation. Alternatively, an implant comprising the composite of the invention is provided. Furthermore, the composite may be used as a cement for or as a coating on synthetic or other implants such as pins and plates, for example, in hip replacement procedures. Thus, the present invention further provides implants or medical devices coated with the matrix of the invention.

In accordance with the invention, provided is the use of the composite of the invention for the manufacture of a medicament for treating diseased or injured bone in orthopedic, periodontal and craniofacial indications wherein the composite is provided alone or comprising therapeutic agents that accelerate the healing rate and enhance the quality of bone formation.

In certain applications, a solid implant is desired. According to one embodiment the present invention a bone substitute composition comprising synthetic apatite and at least one supplementary bioactive agent selected from a biocompatible polymer and an anti-resorptive agent, optionally further comprising a therapeutic agent, optionally further comprising an additive that promotes hardening of said composition in situ over about 10 minutes to about 120 minutes following application. Alternatively, in the reconstruction of structural tissues like cartilage and bone, certain applications may require implantation of a solid implant. This may be achieved by molding or pressing the composition into three dimensional configuration articles of varying thickness and shape in vitro. Accordingly, provided is an implant comprising synthetic apatite at least one supplementary bioactive agent selected from a biocompatible polymer and an anti-resorptive agent, optionally further comprising a therapeutic agent, further comprising an additive that promotes hardening of said composition which may be formed to assume a shape which may constitute a prosthesis. A non-limiting example of a hardener includes calcium sulfate or calcium phosphate compounds. The shape is determined by the shape of a mold or support which may be made of any inert material and may be in contact with the composite on all sides, as for a sphere or cube, or on a limited number of sides as for a sheet.

According to one embodiment of the present invention a composition comprising said synthetic apatite is prepared for administration comprising sterilizing the powder, adding a sufficient amount of liquid to hydrate and disperse the powder, and preparing the wetted powder for administration. Following the wetting procedure the composition may be optionally filtered to remove excess liquid, thus leaving a paste-like material on the filter.

Further provided is a method of preparing the bone-enhancing composite. The method comprises the following steps:

a) preparing a liquid mixture comprising ionic calcium, phosphate, at least one amino acid in either monomeric or polymeric form, carbonate, at least one supplementary bioactive agent selected from a biocompatible polymer and an anti-resorptive agent, optionally further comprising a therapeutic agent;

b) subjecting said mixture to microwave irradiation;
c) quenching said irradiated mixture;
d) filtering said quenched mixture so as to separate between the filtrate and a cake;
e) drying said cake;
f) grinding said cake into a powder.

According to one embodiment of the present invention the above process may further comprise the following steps:
g) sterilizing said powder;
h) wetting said sterilized powder with a solution optionally comprising at least one therapeutic agent;
i) preparing said wetted powder for administration.

The mixture of step a) comprises a calcium ion that may be, for example, calcium chloride added to a concentration of about $5 \times 10^{-3}$ to about $5 \times 10^{-2}$. The phosphate may be a phosphate such as $NaH_2PO$, added to a concentration of about $3 \times 10^{-3}$ to about $2 \times 10^{-2}$. The preferred concentration is about $6 \times 10^{-3}$. The amino acid may be any monomeric or polymeric amino acid but is preferably L-aspartic acid, added to a concentration of about 10 ppm to about 50 ppm. The carbonate may be, for example $NaHCO_3$, added to a concentration of about 1 ppm to about 600 ppm. According to one embodiment, the concentration of carbonate is about 150 ppm. The supplementary bioactive agent is selected from a biocompatible polymer and an anti-resorptive agent.

According to one embodiment of the present invention the powder resulting from step (f) consists of poorly crystalline apatite (PCA) calcium phosphate aggregates having approximately 0.45 µm to about 10 µm in diameter, preferably about 1 µm to about 6 µm in diameter.

The microwave heating step is typically carried out in a standard kitchen 700W-1000W microwave for approximately 10 minutes to about 30 minutes.

The powder of step (f) following autoclave and drying, was shown to be a graft material for filling holes in bones (Ben-Bassat et al, in Biomaterials Engineering and Devices: Human Applications v2, p155-169, 2000). The present invention provides a unique composite with superior properties useful as a bone-enhancing agent in indications where a bone growth or bone enhancement is needed. It is to be understood that the entire process may be scaled up for mass production.

The composition may be sterilized for use in vivo, in particular for use in clinical and therapeutic applications in mammals. The present inventors have shown that the dry synthetic apatite composite powder is sterilizable by ionization, preferably γ-irradiation, and retains its original X-ray diffraction pattern. The powder resulting from step (f) was irradiated at a minimum of 2.5 Mrad according to known GMP production procedures, followed by X-ray diffraction analysis.

Following thermal sterilization, e.g. 140° C. for about 30 minutes to about 2 hours, the X-ray diffraction pattern shows two minor reflections which may be seen at approximately 2θ at about 32.1° and about 32.7°. According to one embodiment of the present invention, a thermally sterilized composite is useful as bone substitute.

According to one embodiment the present invention provides wetting the sterilized PCA powder with a pharmaceutically acceptable liquid such as water or a physiological fluid preferably comprising a growth factor other therapeutic agent. The liquid is added in a sufficient amount to allow wetting and dispersion of the powder to form a wetted mixture having the consistency of a paste or putty. In one embodiment of the present invention the powder is mixed with liquid, such as PBS or hyaluronic acid solution, in a ratio of about 1:1 w/w or w/v to yield a paste-like substance. In one particular exemplary embodiment 0.3 gm powder is mixed with 0.3 ml sterile water comprising growth factor, in particular an FGF or FGF variant to yield approximately 0.5 ml paste-like composition.

Alternatively, a sufficient amount of liquid is added to permit wetting and dispersion of the powder to form a hydrated precursor mixture having a consistency compatible with application to a filtration device. The wetted powder is filtered through a sterile filtration device having pore size enabling retention of the crystalline aggregates on the filter. Preferably, the pore size of the filtration device permits full retention of the bone substitute material. In one particular exemplary embodiment 0.3 gm synthetic apatite composite are mixed with 2 ml sterile PBS comprising a growth factor, in particular an FGF or FGF variant. The mixture was left for 1 hour to allow the FGF to adsorb to the composite and the slurry filtered through a 0.45 µm filter to yield approximately 0.5 ml paste-like material.

The filtered material is left sufficiently wetted in order to enable handling without fragmentation or crumbling or separation of the liquid from the solid phase. Preferably the wetted powder has a consistency of putty or paste. Preferably the paste has a viscosity in the range of about 10 poises to about 500 poises, preferably about 30 poises to about 200 poises.

In another embodiment of the present invention, the wetted powder is blended under sterile conditions to a consistency compatible with administration to a lesion. The paste may be administered manually or with a spreading instrument such as a spatula. More preferably, the wetted powder is inserted into a syringe and is prepared for local administration or injection into the site of the defect or lesion.

The term "therapeutic" refers to any pharmaceutical, drug or prophylactic agent which may be used in the treatment (including the prevention, diagnosis, alleviation, or cure) of a malady, affliction, disease or injury in a patient.

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, or gelatin. Pharmaceutical compositions may also include one or more additional active ingredients.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

The term "physiologically acceptable liquid carrier" or "diluent" refers to an aqueous or non-aqueous fluid that is well suited for pharmaceutical preparations.

The composite of the experiment may be used in particle or powder form, or may be combined with a physiological liquid for use as a paste-like material. The composition may further comprise hardening agents for in situ or in vivo hardening. Alternatively an implant comprising the composite of the invention is provided. Furthermore, the composite may be used as a coating on synthetic or other implants such as pins and plates, for example, in hip replacement procedures. Thus, the present invention further provides implants or medical devices coated with the matrix of the invention.

According to an alternative embodiment the pharmaceutical composition further comprises at least one agent that renders the composition non-fluid under physiological conditions. A non-limiting example of a collagen that gels at physiological temperatures is disclosed in WO 00/47130.

Bone Repair

Fractures and other defects in long bones heal via a process known as endochondral ossification while defects and lesions in intramembranous bones heal via an osteogenic route (Rabie, et al., Int J Oral Maxillofac Surg 25(5):383, 1996). Four stages of fracture repair have been characterized (reviewed in Bolander, Proc. Soc. Exp. Biol. Med. 200(2): 165, 1992). Stage 1 is the immediate injury response; stage 2 marks the synthesis of new bone matrix and callus formation in a process termed intramembranous ossification; stage 3, designated chondrogenesis, occurs as the mesenchymal cells develop into chondrocytes and are eventually replaced by cartilage; stage 4 is the formation of bone from cartilage in a process known as endochondral ossification.

According to the principles of the present invention the composite of the invention is useful in indications where bone enhancement and bone healing is desired. According to one embodiment the composite of the invention is useful in orthopedic indications including periodontal surgery, and plastic and craniofacial surgery. In a non-limiting example, the composite of the present invention is useful for augmentation of the alveolar ridge to facilitate retention of denture and to fill various periodontal lesions. It is also useful to fill the gap in cases of bony defects, cysts and traumatic bone loss. The composite of the present invention is useful for maxillofacial dysplasia, filling of bone defects in skull, zygomatic and mandibular areas and augmentation of various bony areas. In addition, the composite of the present invention is useful to reconstruct the calvaria including repair of cranial base and temporal bone defects following surgery. Orthopedic applications in which the compositions of the invention are useful include, but are not limited to, fractures and non-union fractures resulting from a trauma or generated by surgical means, spinal fusion, hip resurfacing or bone augmentation in indications such as osteopenia or osteoporosis.

According to the principles of the present invention the composite comprises therapeutic agents that have the capacity to act at some or all of the stages in order to enhance bone repair and ensure the formation of functional bone.

The present invention further provides use of a composite comprising synthetic apatite and at least one supplementary bioactive agent selected from a biocompatible polymer and an anti-resorption agent added ab initio, wherein the synthetic apatite comprises ionic calcium, phosphate, carbonate and at least one amino acid in monomeric or polymeric form for the manufacture of a bone-enhancing medicament.

Kits

The present invention further provides a kit comprising the composite of the present invention, where the dry and liquid components may be present in separate containers in the kit, or some of the components may be combined into one container.

The following examples are intended to be merely illustrative in nature and to be construed in a non-limitative fashion.

EXAMPLES

Example 1

Preparation of Bone Raft Powder

A method for preparation of a bone substitute is disclosed in U.S. Pat. No. 6,231,607. The bone substitute prepared by this method has an X-ray diffraction pattern similar to natural bone. The present inventors now disclose that at least one supplementary agent such as a biocompatible polymer and/or an anti-resorptive agent as may be added during the formation of the synthetic apatite crystals. The powder can be used per se or formulated into a fluid composition having advantageous properties for use as a bone graft material.

Materials and Methods

Graduated bottles, 2-liter capacity and 500 ml capacity

Glass ice bath

Microwave Oven (700W)

Vacuum Filter

Millipore Filter 0.45 μm-9 cm diameter Z29078-5 (Sigma)

Microwave oven

Trizma buffer PRE-SET Crystals Type 7.4-FT (Sigma)

Sodium dihydrogen phosphate monohydrate $NaH_2PO_4 \cdot H_2O$ (MERCK)

Sodium Bicarbonate $NaHCO_3$ (ICN)

L-Aspartic Acid monosodium salt (Sigma)

Calcium Chloride Dihydrate $CaCl_2 \cdot 2H_2O$ (MERCK)

DDW/TDW, Filtered.

Two solutions were prepared:

Solution I ($CaCl_2$+Trizma+supplementary agent): 20.0 gr. Trizma, 2.94 gr. $CaCl_2$, polymer, 2.0 liters of DDW.

Solution II ($NaH_2PO_4$+Trizma): 20.0 gr. Trizma, 1.66 gr $NaH_2PO_4 \cdot H_2O$, 0.6 gr. $NaHCO_3$ 0.1 gr. L-Aspartic Acid, 2.0 liters of DDW.

Equal volumes of solution I and solution II (1.5 liters each) were mixed rapidly in a 4 liter glass bowl. The final solution had the following concentrations: 0.01 M $CaCl_2$, 0.006 M $NaH_2PO_4$, 150 ppm (mg/Liter) $NaHCO_3$, 25 ppm L-Aspartic Acid with varying concentration of biocompatible polymer or anti-resorptive agent.

The solution was heated in a microwave oven at maximum power for 30 min.

The irradiated mixture was placed in an ice bath for 1 hr.

The mixture was filtered through a Millipore filter (0.45 μm).

The precipitate was washed with 50 ml of DDW.

The precipitate was transferred to a glass beaker and dried overnight at about 55° C.-60° C.

The dried precipitate was ground to a fine powder using a mortar and pestle.

The resulting powder was weighed for quantity determination.

The powder was sterilized by γ irradiation.

The powder was stored in a closed 15 or 50 ml screw capped vials and labeled according to date, batch number and quantity.

The supplementary bioactive agents were added to solution 1 in the amounts presented in Table 1. The quantities listed do not represent the final concentration but rather the amounts added to the starting solution.

TABLE 1

| Supplementary agent | ug/ml (microgram/ml) | | | | | | | | | |
|---|---|---|---|---|---|---|---|---|---|---|
| Heparin 15 kDa | 100 | 50 | 5 | | 0.5 | | | | | |
| Heparin 6 kDa | 100 | 50 | 5 | 1 | 0.5 | 0.25 | 0.1 | 0.05 | 0.001 | 0.0001 |
| SOS | | | 3.33 | 0.33 | 0.033 | | | | | |
| Dex Sulfate | | | | | 1 | | | | | |
| Alendronate, acid | | | | 1 | 0.1 | | | 0.001 | | |
| Alendronate, Sodium salt | | | | 1 | 0.1 | | | 0.001 | | |

Heparin -MW 15 kDa; heparin-MW 6 kDa; sucrose octasulfate (SOS) MW-1.16 kDa; dextran sulfate MW 10 kDa. The composites are tested in adsorption, resorption and release assays, in X-ray diffraction and FITR. (kD or kDa refers to kilodalton)

Example 2

X-Ray Diffraction Analysis

Figure 1B:
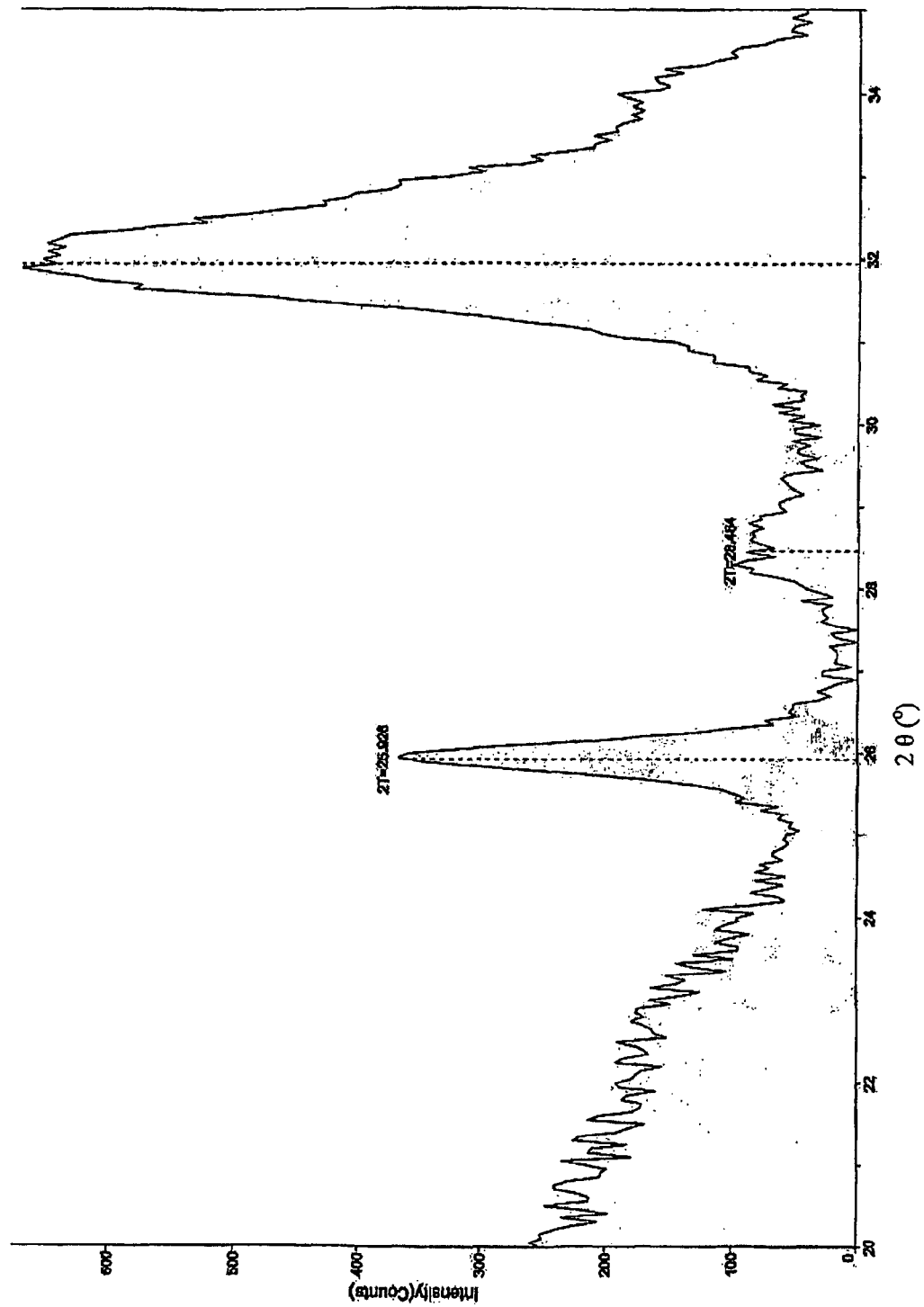
Figure 1C:
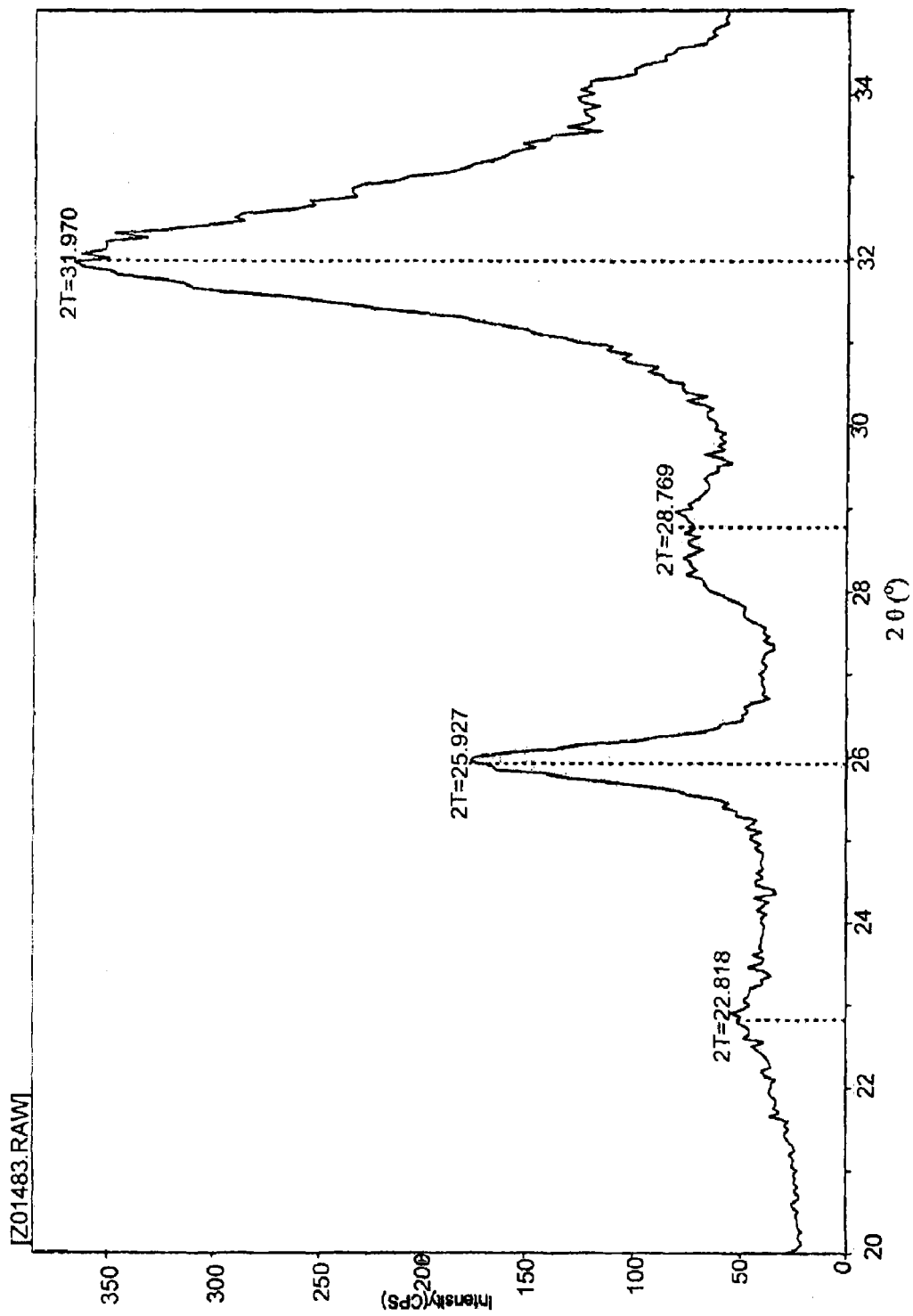
Figure 1D:
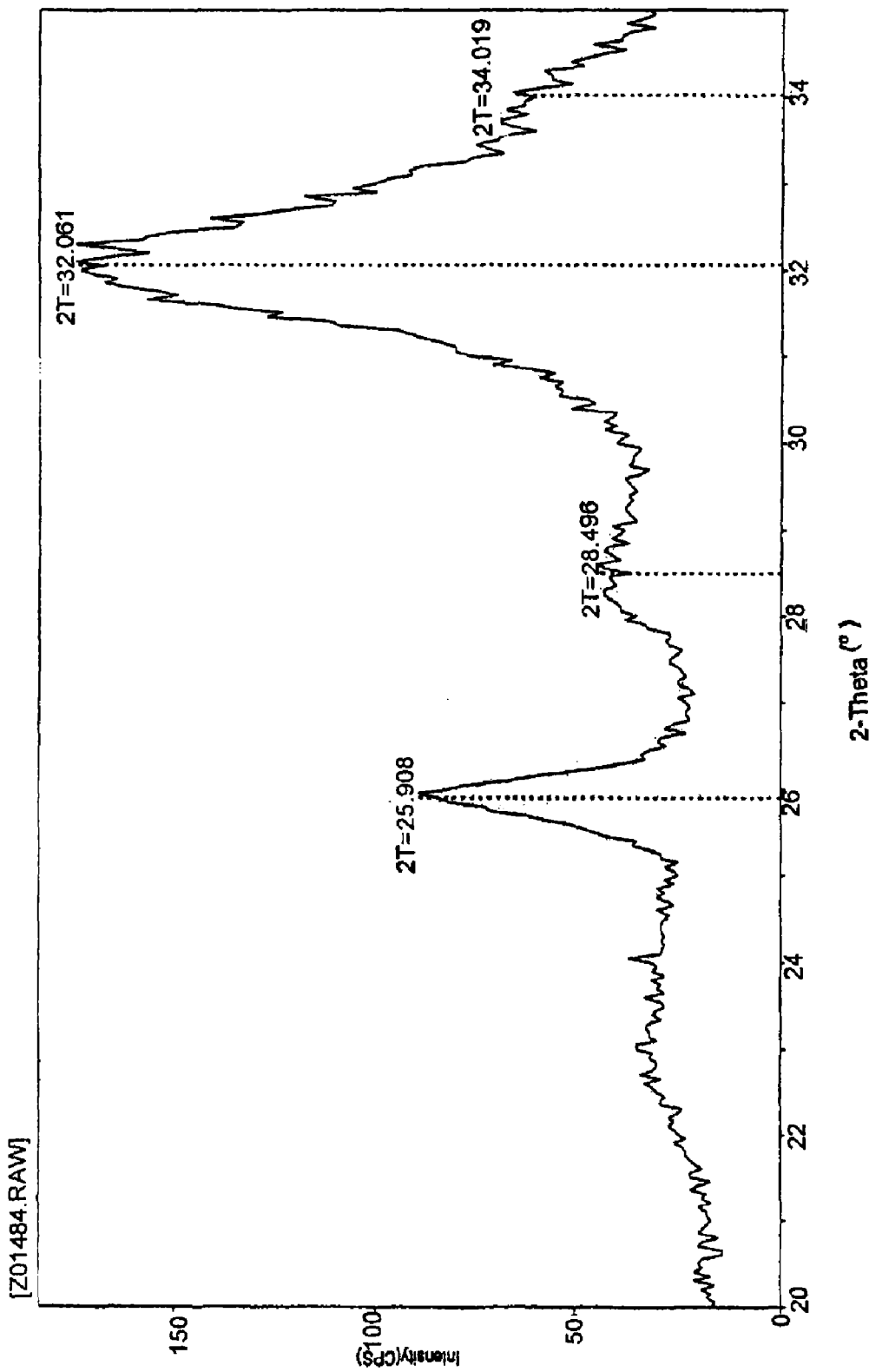
Figure 1E:
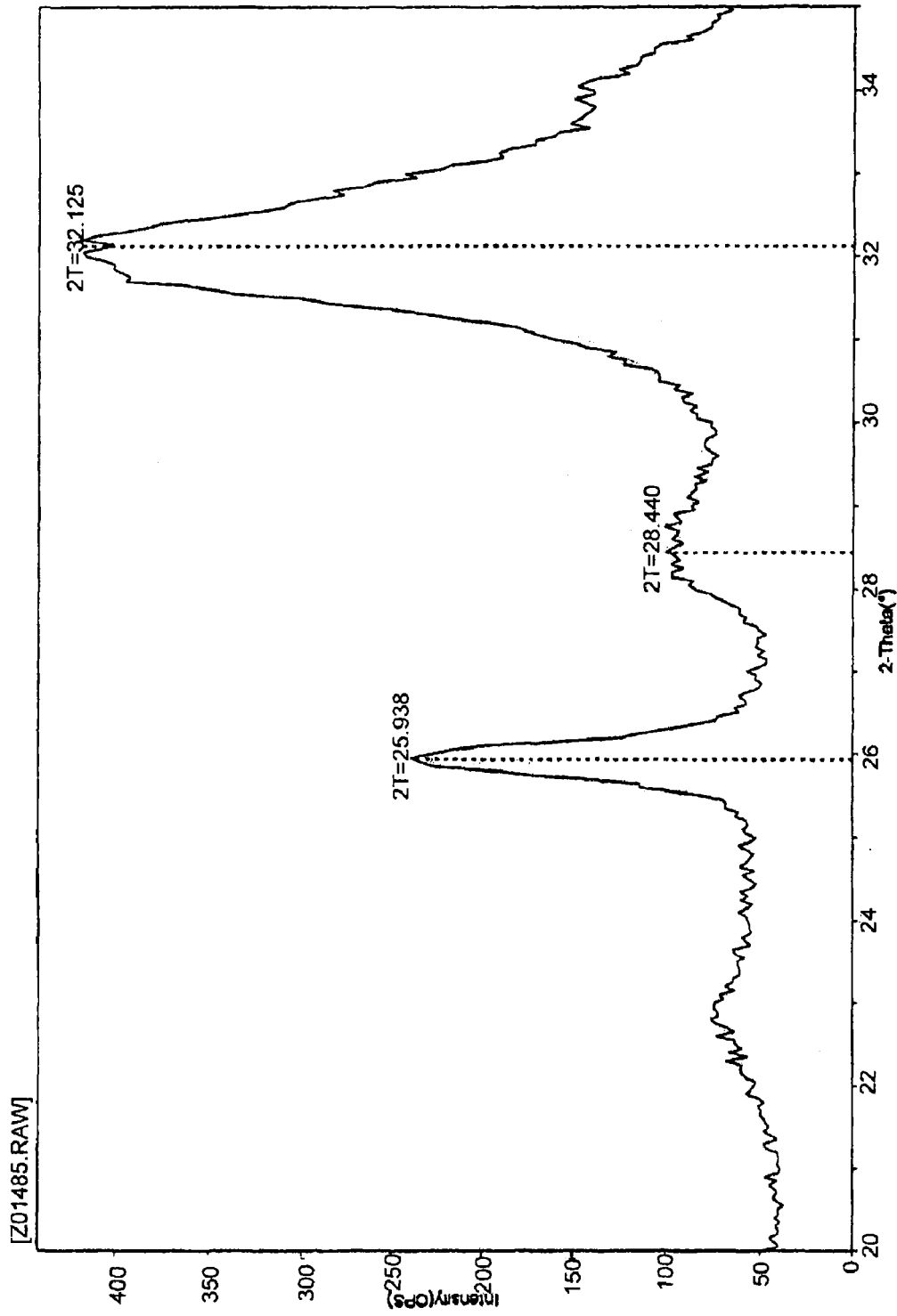

Bone substitute, material prepared according to U.S. Pat. No. 6,231,607 and composite prepared according to Example 1 and sterilized by heat sterilization or γ-irradiation was exposed to X-ray. An X-ray diffraction (XRD) pattern was obtained from a packed powder sample of the material pulverized in a mortar and pestle. X-rays were performed using an X-ray powder diffractometer, Rigaku, Japan. The scan rate was set to 0.5 degree/minute over the 2 theta (2θ) angular range from 20°-35°. The step size was set to 0.05°. FIG. 1A shows the X-ray diffraction pattern of the bone substitute powder prepared according to U.S. Pat. No. 6,231,607. A peak at 2θ about 26° and a large undifferentiated peak at 2θ about 31° to about 33° are noticeable. The X-ray diffraction pattern of a composite comprising heparin, wherein the heparin was added to 0.5 parts ug/ml is presented in FIG. 1B. The X-ray diffraction pattern of a composite comprising dextran sulfate added to 0.5 ug/ml is shown in FIG. 1C. The X-ray diffraction patterns of composites comprising sucrose octasulfate added to 0.5 or 5 ug/nl are shown in FIGS. 1D and 1E, respectively. In all the cases the X-ray diffraction patterns of the composites show strong similarity to the unradiated material, specifically a characteristic peak at 2 theta of about 25.5° to about 26° and an undifferentiated peak at 2 theta 2θ of about 31° to about 33°.

Figure 1F:
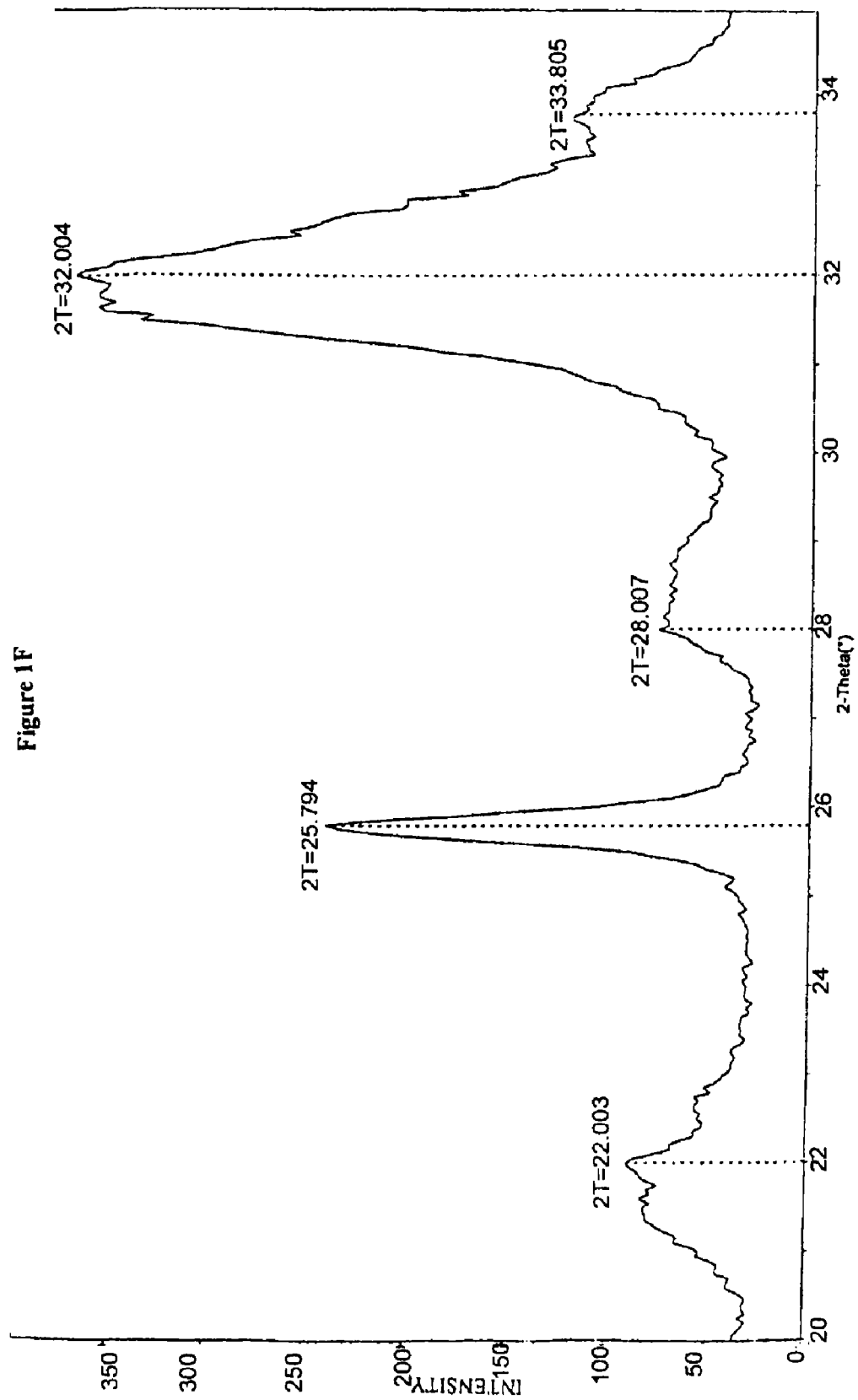
Figure 1G:
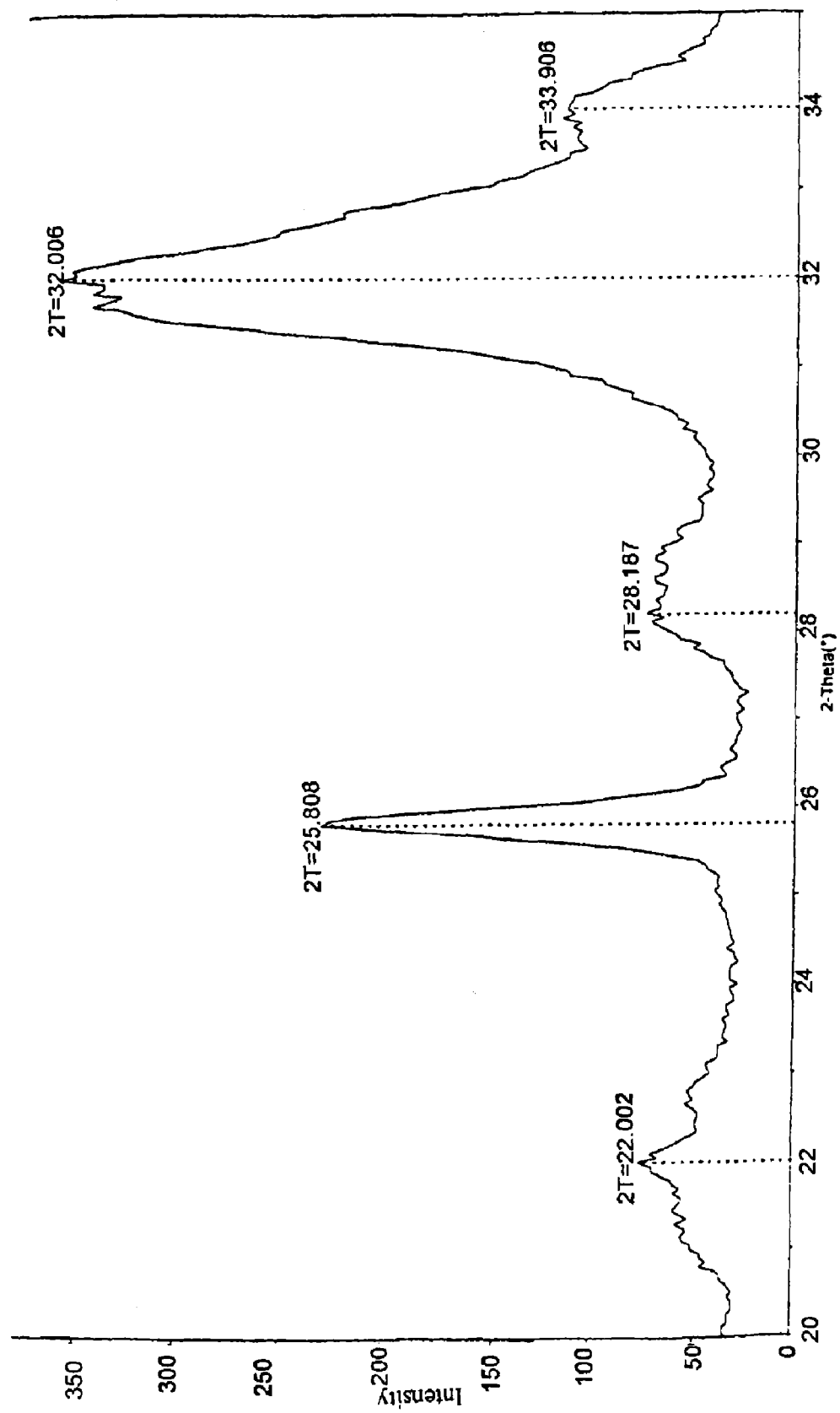
Figure 1H:
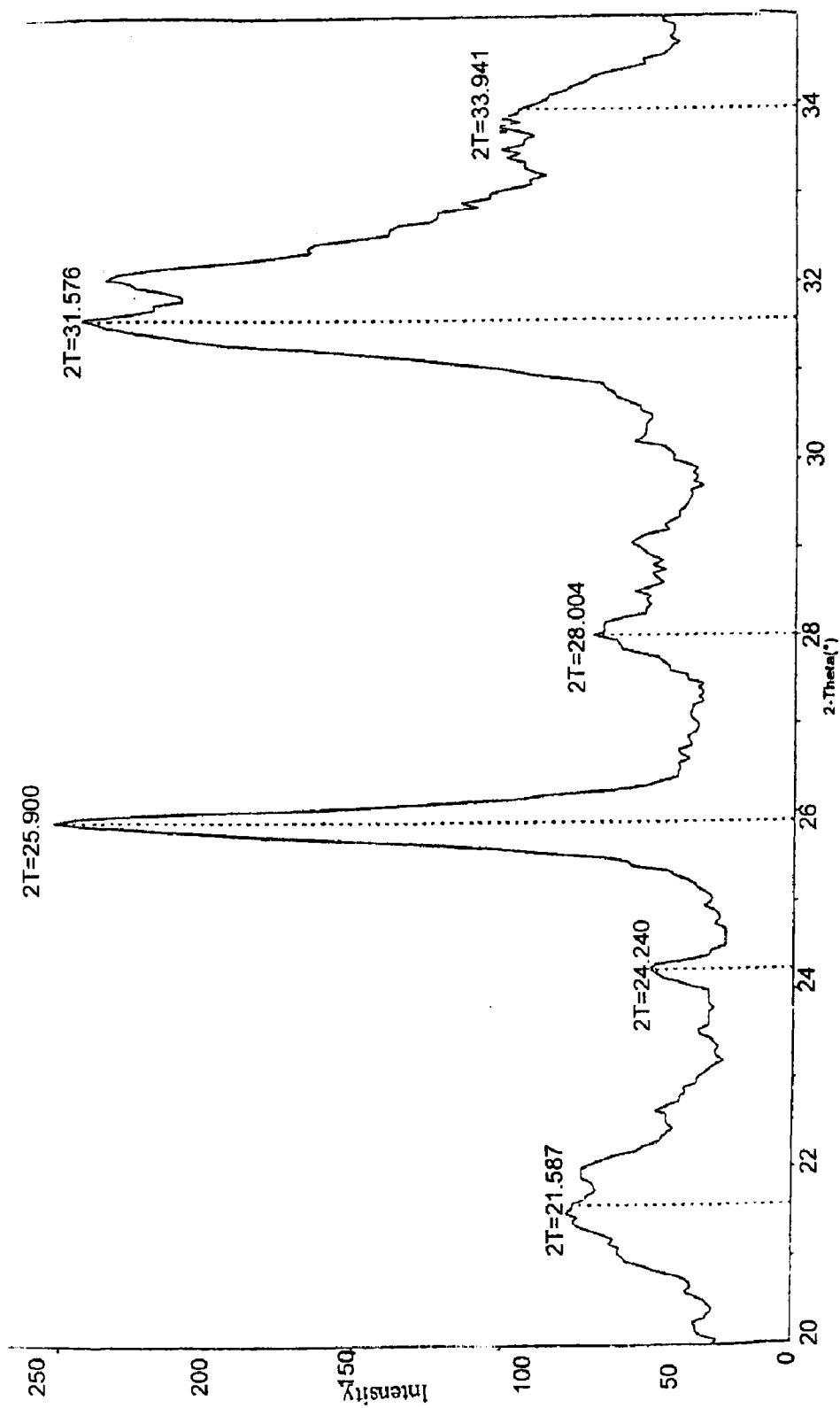

The X-ray diffraction pattern of a composite prepared with 0.0005 ug alendronate/ml is presented in FIG. 1F. The acid form and the sodium salt form gave identical results. The X-ray diffraction pattern of a composite prepared with 0.05 alendronate or 0.5 ug alendronate/ml are shown in FIGS. 1G and 1H respectively. The composite comprising the higher concentration of alendronate (0.5 ug/ml) exhibits a high crystallinity pattern with an additional peak at 2 theta 2θ=24.24° and a larger peak around 2 theta 2θ=25.9°.

Example 3

Scanning Electron Microscope Analysis

Figure 2A:
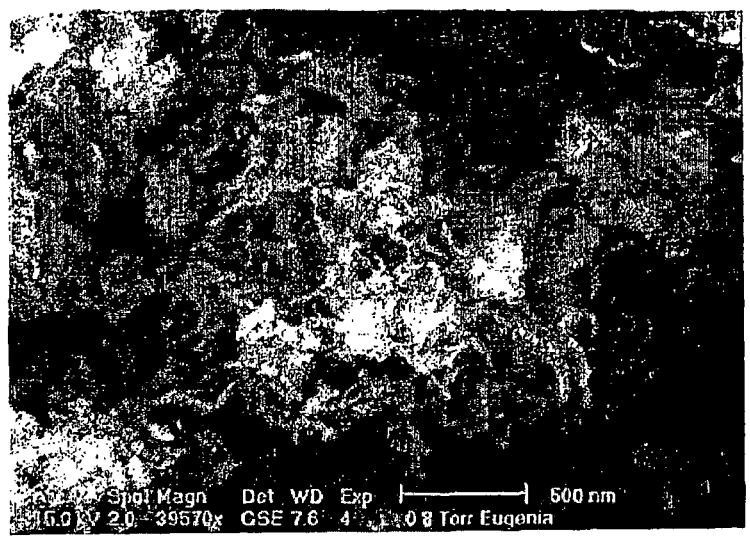
FIG. 2A shows bone-enhancing material without additives.
Figure 2B:
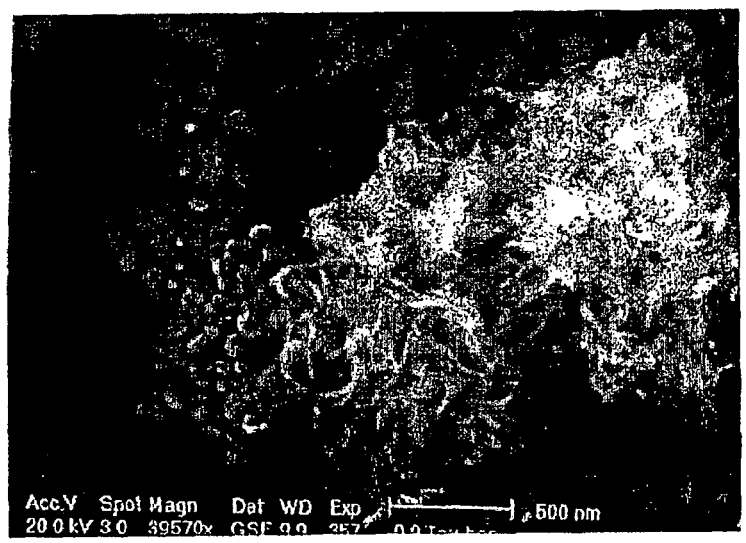
FIG. 2B shows synthetic apatite-heparin (0.5 ug/ml) composite.
Figure 2C:
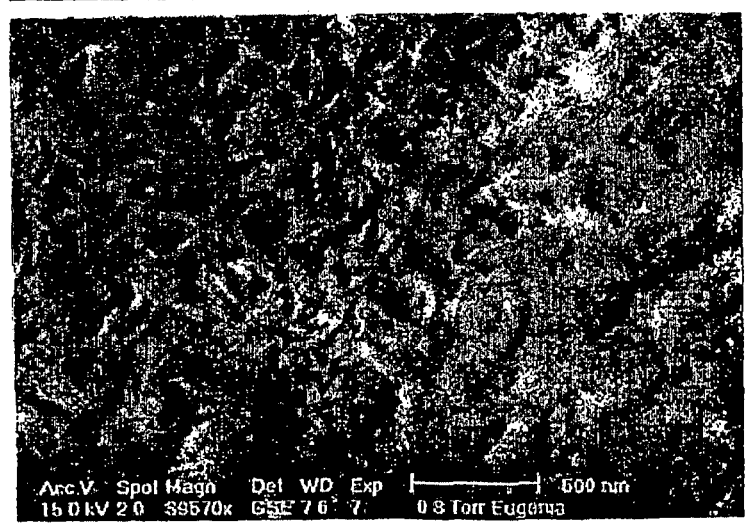
FIG. 2C shows synthetic apatite-heparin (100 ug/ml) composite. All figures are 39570× magnification.

Bone substitute composites prepared with various amounts of different polysaccharides was subject to Scanning Electron Microscope Analysis (SEM). FIGS. 2B and 2C show the aggregate formation of the synthetic apatite-heparin composite (0.5 ug/ml and 100 ug/ml, respectively) as compared to the synthetic apatite (PCA) alone shown in FIG. 2A. The composite prepared from the liquid mixture comprising 0.5% W/W Heparin MW 6,000 exhibited a distinct structure as seen by SEM. All figures are 39570× magnification.

Example 4

Bone Substitute Composite with a Poloxamer Copolymer

Pluronic® is a block co-polymer that may serve to impart select physical and biological properties to the composite, serves as a hemostatic agent. The formation of this system is carried out essentially following the steps as for the biocompatible polymers exemplified above.

The synthetic apatite-heparin composite was mixed with varying concentrations of Pluronic, 1:500 to about 1:16,000 weight ratios of Pluronic to composite. 100 µl rod shaped structures of the blend, comprising an FGF (5 and 10 µg/ml), were examined for FGF release in a FDCP assay. At concentrations of 1:2000 and less Pluronic had no detrimental effect on cell proliferation activity of FGF. The composition is further tested in animal models of fracture healing.

Example 5

Resorbability Assay

Assays for determining the rate of in vivo biodegradability include intramuscular, subcutaneous and intraosseous models. An in vivo assay measuring subcutaneous resorption of dense carbonate apatite is disclosed in Barralet (Barralet, J. et al., J Biomed Mater Res 49(2):176-82, 2000). Another example discloses the resorption of porous ceramic implants in a dog model (Pollick, S., et al., J Oral Maxillofac Surg, 53(8):915-22; 1995). Other in vivo assays include those that are presented in Example 10 herein.

Example 6

Semi-Fluid Composition

These examples demonstrate the methods of preparing a semi-fluid composition for use as a bone enhancing material.

An amount of 0.3 gm dry sterile powder of Step 1 was mixed with 2 ml sterile PBS. The composition was mixed for 1 hour on a shaker and filtered through a 0.45 µm membrane to remove excess liquid. Remaining on the filter was approximately 0.5 ml of a pasty substance that was placed into a syringe for local administration in an animal model, for example as is described in example 10, vide infra.

An amount of 3 gm dry sterile powder of Step 1 was mixed with 3 ml sterile PBS to yield approximately 5 ml of a pasty substance that was placed into a syringe for local administration in an animal model.

Additional compositions are prepared by varying the w/w or w/v ratio of the composite and a pharmaceutically acceptable diluent including hyaluronic acid. Viscosity of the fluid or semi-fluid compositions was determined by standard techniques.

Example 7

FGFR-Transfected FDCP Proliferation Assay

This assay was used to determine the release of FGF from the composite comprising the synthetic apatite and a polymer, specifically heparin, SOS or dextran sulfate.

The FDCP cell line is a murine immortalized, interleukin 3 (IL-3)-dependent cell line of myelocytic bone marrow origin that does not express endogenous FGF Receptors (FGFR). Upon transfection with FGFR cDNA, the FDCP cell line exhibited a dose-dependent proliferative response to FGF that replaces the dependence on IL-3. FGFR transfected FDCP cells can therefore be used to screen for FGFR signaling. The cell response to various ligands is quantitated by a cell proliferation assay with XTT reagent (Cell Proliferation Kit, Biological Industries Co.). Specifically, FDCP cells stably expressing the FGFRI (FDCP-FGFRI) were grown in "full medium" (Iscove's Medium containing 2 ml glutamine, 10% FCS, 100 ug/ml penicillin, 100 ug/ml streptomycin) supplemented with 5 ug/ml heparin. Cells were split every 3 days and kept in culture no more than one month. One day before the experiment the cells were split. Before the experiment the cells were washed 3 times (1000 rpm, 6 min) with full medium. The cells were resuspended and counted with Trypan Blue. Twenty thousand ($2 \times 10^4$) cells were added to each well of 96-well plate in 50 µl full medium containing heparin. Condition medium containing FGF or FGF complexed with the various polysaccharides was added in an additional volume of 50 µl full medium to bring the final volume to 100 µl. The plate was incubated for 48 hours at 37° C. To test cell proliferation, 100 µl of PMS reagent was added to 5 ml of XTT reagent and mixed well (according to manufacture protocol). 50 µl of the latter solution were aliquoted into each well, and the plates incubated at 37° C. for at least 2 hours and the color developed was read by a spectro-ELISA reader at $A_{490nm}$.

Example 8

Release of FGF from the Composite

Certain FGF molecules were used as the therapeutic agent and both the synthetic apatite and synthetic apatite-heparin composite were tested as carriers.

An FGF (FGF2, 200 µl of a 1, 10 or 20 um/ml solution) was added to 50 µl of dry synthetic apatite and synthetic apatite-heparin composite and allowed to adsorb for 1 hour at room temperature (RT). The synthetic apatites were centrifuged, the supernatant removed, and washed with 1×PBS. Two independent assays were performed on this material. An ELISA, as described in example 9, was carried out to establish the total amount of FGF that bound to the synthetic apatite and synthetic apatite-heparin composite. An FDCP proliferation assay, as described in example 7, was carried out to determine whether the FGF bound to the material remained active.

FIG. 3A shows the amount of FGF that was able to bind to either the synthetic apatite prepared according to U.S. Pat. No. 6,231,607 (PCA) and the various synthetic apatite-polymer composites as determined by direct binding ELISA.

Figure 3C:
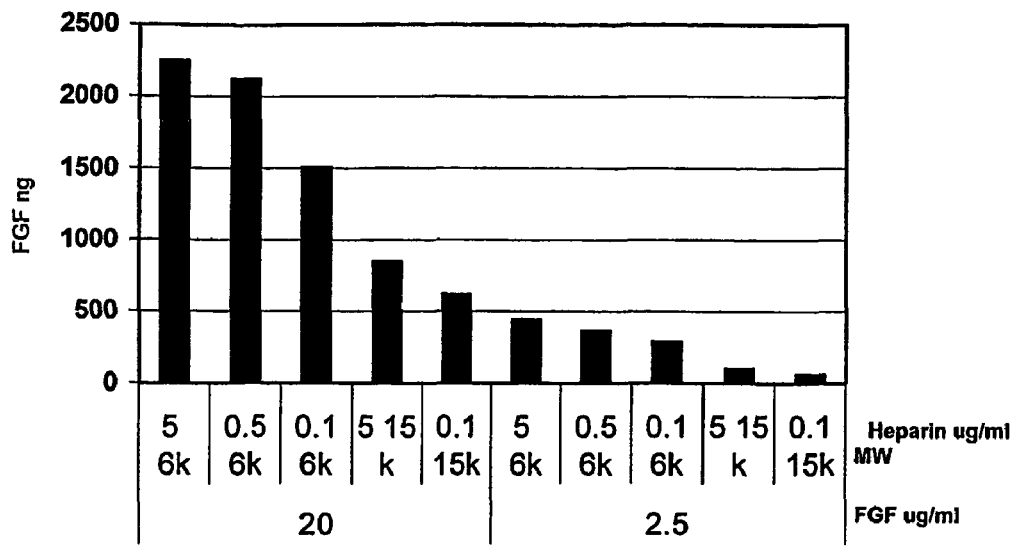
FIG. 3C shows release of FGF from synthetic apatite-heparin composites after 3 days.
Figure 3D:
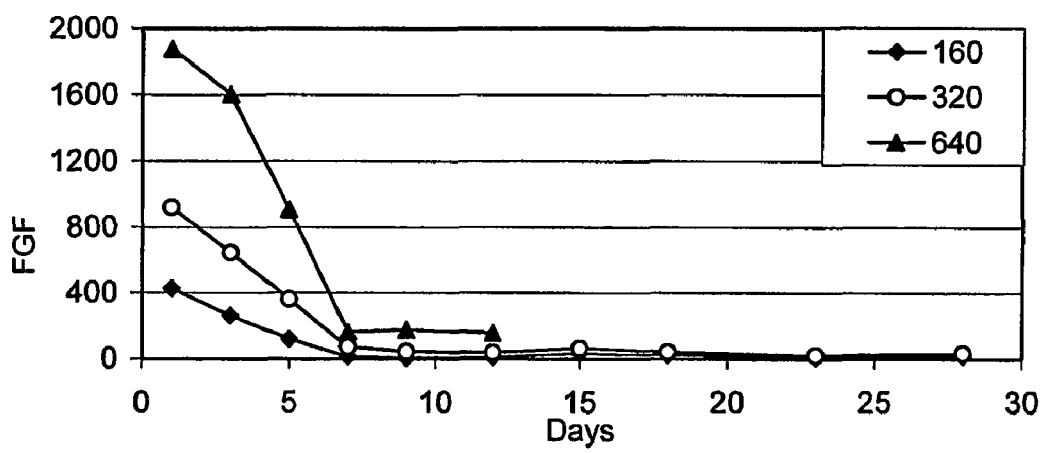
FIGS. 3D and 3E show sustained release of FGF from synthetic apatite-heparin composites.
Figure 3E:
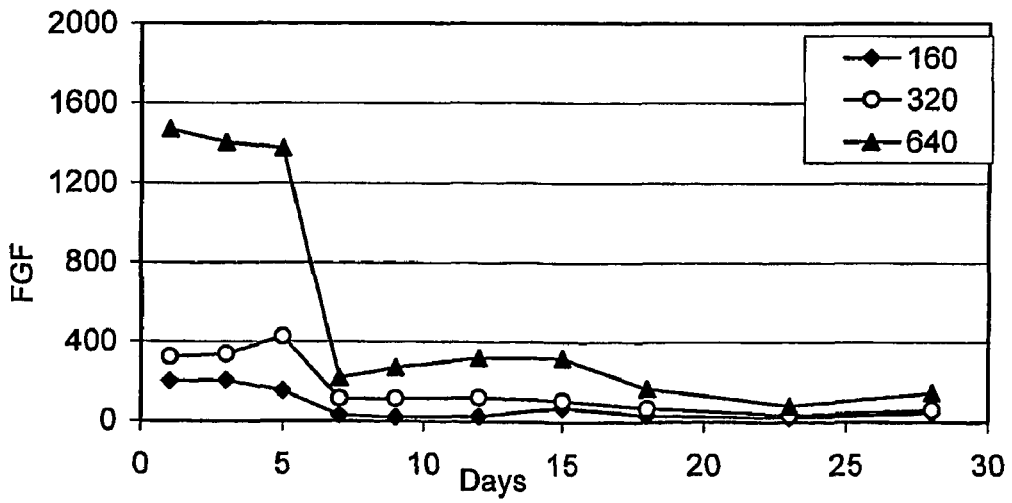

FIG. 3B shows the results of the proliferation assay of FGFR1 expressing FDCP cells in the presence of composite comprising FGF and suggests that the amount of FGF released and the rate of release from the composite depended on the type of polymer incorporated into the composite. SOS refers to the synthetic apatite-polymer composite comprising SOS (0.5 ug/ml added ab initio). The dextran adsorbed FGF quite poorly (>5%) and it appears that the FGF was released in a regular manner, albeit in small doses. A majority of the FGF that bound was released within the first day. "hep" refers to the synthetic apatite-heparin composite comprising heparin (MW 6,000; 0.5 ug/ml). A large proportion of the FGF added to the composite was adsorbed by the composite (85%) and the amount of FGF released was spread out over the 7 weeks of the assay. This results suggests that the synthetic apatite-heparin composite provides a good delivery system for controlled release of FGF. It will be apparent to a person with skill in the art that different polysaccharides, preferably glycosaminoglycans including heparin derivatives, including very low molecular weight heparin, low molecular weight heparin, heparin derivatives and heparin mimetics may be used in place of the heparin tested herein to control release of specific growth factors to different tissue types. The synthetic apatite itself showed reduced release of FGF over time, despite the fact that 20% of the FGF added was adsorbed to the material. FIG. 3C shows the release of an FGF from a composite comprising heparin of different molecular weights and concentrations. Greater amounts of FGF are released from a composite comprising a low molecular weight heparin (6 kD) at higher concentration (0.5-5 ug/ml) than from high molecular weight heparin (15 kD). Different composites may be beneficial for different applications and indications. FIGS. 3D and 3E show the release profile of FGF (160, 320 or 640 ug/ml) from synthetic apatite-heparin composites, comprising either 0.5 ug/ml heparin (3D) or 5 ug/ml heparin (3E). The rate of release of a therapeutic agent the composite may be optimized for different applications and tissue types. For example, endochondral bone formation may benefit from a different release pattern of FGFs that intramembranous bone formation. In infected tissue, fast release of an anti-microbial and slow release of a growth factor may enhance healing.

Example 9

Direct Binding ELISA

This assay was performed to quantify the binding of a therapeutic agent to the poorly crystalline apatite or to the synthetic apatite and a polymer composite.

For the ELISA assay, 50 ul of sample was dissolved in 1 ml of 250 mM EDTA for 5-7 hours at RT with shaking and measured as follows:

The wells of the plate were coated with an FGF/sodium bicarbonate solution. A calibration curve was prepared for FGF concentrations in the range of 250 ng/ml to 8 ng/ml. Dilutions of test-samples (PCA or PCA-derivative adsorbed with a therapeutic agent) were prepared in bicarbonate-buffer to get a final concentration of 0.1 M bicarbonate. The dilutions of the test samples were in a range so that the predicted concentration of FGF fell in the linear area of the calibration.

To each well of a 96 well plate (NUNC immunoplate, F96 maxisorp) 100 µl of each test sample was added. The plate was covered with Parafilm™ and incubated at 4° C. overnight (ON). The wells were washed with 2M NaCl once and with PBS twice. Detection was carried out as follows: the wells were blocked with 2% BSA by adding 300 µl 2% BSA to each well. The samples were incubated for 1 hour at room temperature (R.), or at 4° C. ON. The wells were washed five times with 300 µl PBST (0.5 ml Tween-20 to 500 ml PBS). The antibody, 100 µl of DG2 (anti FGF2 1:5,000) was added to each well except control. The samples were incubated 2 hours at RT and washed thrice with PBST. One hundred microliter (100 µl) secondary antibody (HRP-conjugated Goat α mouse 1:10,000) was added to each well followed by 3 washes with PBST. TMB substrate (100 µl) was added to each well and the samples incubated at RT until the desired color developed, after about 10 min. and the reaction stopped by adding 50 µl 1 M $H_2SO_4$ to each well. The plate was read in an ELISA spectrophotometer at $A_{450nm}$.

Example 10

Rat Tibia Model

Objectives: To investigate bone in-growth using the bone enhancing composites of the present invention. In some examples the composite was compared to a commercially available ceramic. SA refers to the synthetic apatite alone, SA-hep refers to the synthetic apatite-heparin composite, SA-SOS refers to the synthetic apatite-SOS composite.

Surgical procedure: Animals were anesthetized according to a standard protocol, using intramuscular (IM) injection of 85 mg/kg ketamine and 3 mg/kg hyaline. A defect was created in the proximal tibial metaphysis, 3-4 mm below the collateral ligament insertion, by drilling a hole of 2 mm diameter and 2-3 mm in depth or by cutting a wedge of approximately 1.5 mm deep and 3 mm wide.

The defect was treated according to the treatments listed in the tables below by locally administering various amounts of the synthetic apatite or synthetic apatite composites of the invention using a 1 ml syringe or applying a paste.

Quality evaluation: at the end of the experimental procedure, generally 4-8 weeks, rats were sacrificed and the defect area evaluated histologically for gross cell morphology, cell abundance and the appearance of extra-cellular material. Standard histological staining methods were used (H&E) and the tissue samples were scored by a pathologist for evaluation of histological changes during the healing process.

The following tables show the experimental setup of exemplary trials.

Experiment 1 outlined in Table 2 shows the setup of an 8 week experiment in rats having a wedge defect introduced into the tibia. The effect of SA alone was compared to the effect of SA-SOS composite and a SA-SOS composite (SOS, 0.5 ppm) further comprising an FGF variant (FGF2v).

TABLE 2

| No. | tag | LT leg | RT leg |
|---|---|---|---|
| 1 | No tag | No treatment | No treatment |
| 2 | Tail cut | SA | SA |
| 3 | RT ear cut | SA + SOS | SA + SOS |
| 4 | V in ear | SA + FGF2v | SA + FGF2v |
| 5 | V in ear | SA + FGF2v | SA + FGF2v |
| 6 | Lt ear cut | SA + SOS + FGF2v | SA + SOS + FGF2v |
| 7 | Lt ear cut | SA + SOS + FGF2v | SA + SOS + FGF2v |

Figure 4A:
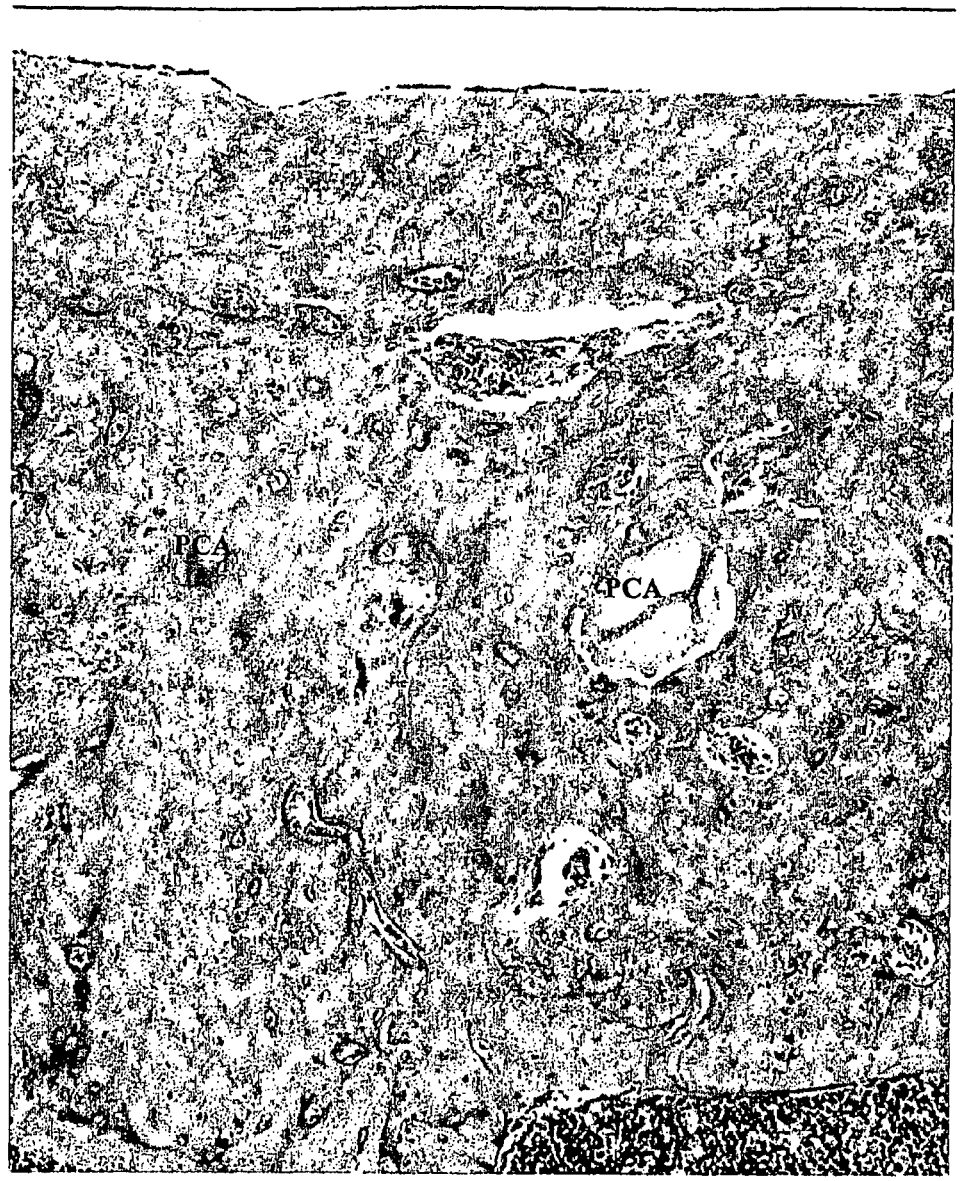
FIGS. 4A and 4B show histological sections of new bone formation in a rat tibia model using a synthetic apatite-SOS composite.
Figure 4B:
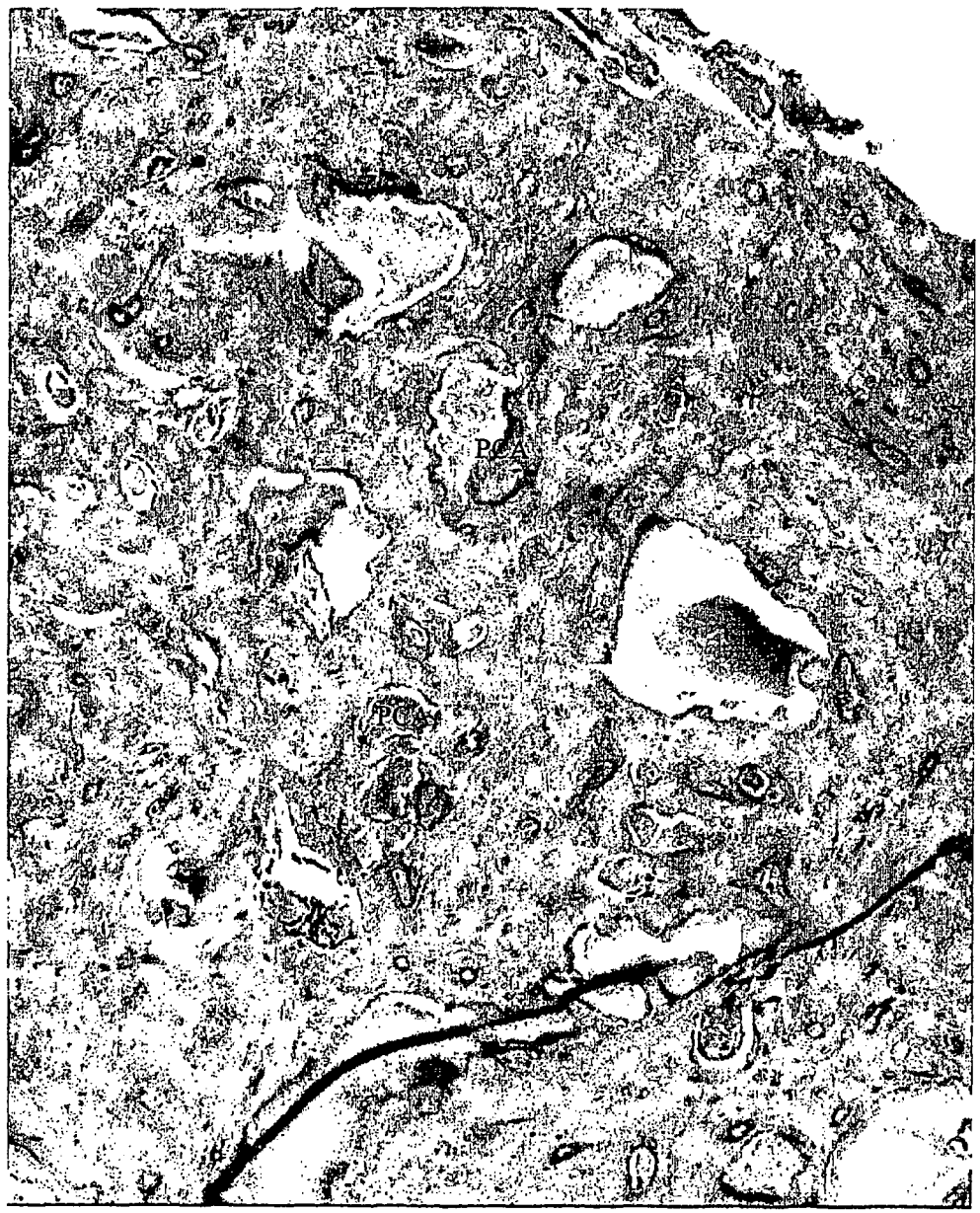

FIG. 4A shows the filling in of the wedge defect with new bone surrounding the SA particles. FIG. 4B shows the bone repair surrounding the SA-SOS aggregates. FIG. 4B shows the presence of more SA-SOS particles remaining in the wedge suggesting that the composite has better cohesive properties than the SA alone. The new bone is developing around the SA-SOS particles suggesting that a composite of the present invention comprising synthetic apatite and sucrose octa sulfate (SOS) is a good quality bone enhancement material.

3) Experiment 2 outlined in Table 3, was designed to test the effect of different concentrations of FGF in a synthetic apatite-heparin composite in a rat tibia wedge model.

TABLE 3

| No. | Tag | Lt leg | Rt leg |
|---|---|---|---|
| 1-2 | No tag | SA + HEP | SA + HEP |
| 3-4 | Tail cut | SA + HEP + 0.04 µg FGFV | SA + HEP + 0.04 µg FGFV |
| 5-6 | LT ear cut | SA + HEP + 0.2 µg FGFV | SA + HEP + 0.2 µg FGFV |
| 7-8 | RT ear cut | SA + HEP + 1 µg FGFV | SA + HEP + 1 µg FGFV |
| 9-10 | 2 ears | SA + HEP + 0.2 µg FGFV | SA + HEP + 0.2 µg FGFV |
| 11-12 | No tag | SA + HEP | SA + HEP |
| 13-14 | Tail cut | SA + HEP + 0.04 µg FGFV | SA + HEP + 0.04 µg FGF2V |
| 15-16 | Lt ear cut | SA + HEP + 0.2 µg FGFV | SA + HEP + 0.2 µg FGFV |
| 17-18 | Rt ear cut | SA + HEP + 1 µg FGFV | SA + HEP + 1 µg FGFV |

Figure 5A:
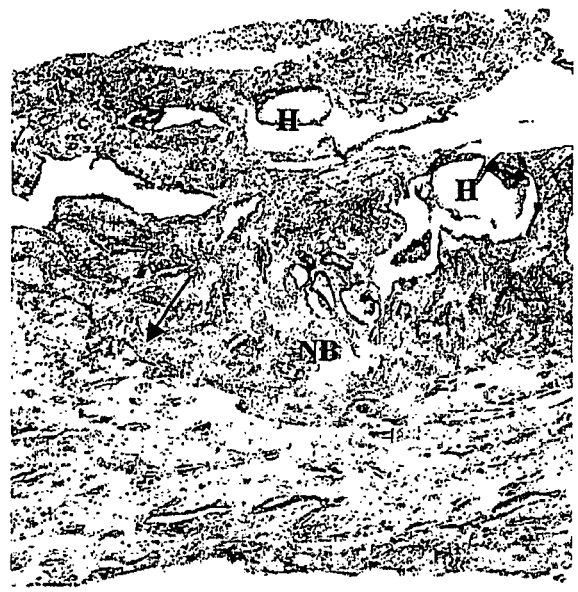
FIGS. 5A and 5B show histological sections of new bone formation in a rat tibia model using a using a synthetic apatite-heparin composite.
Figure 5B:
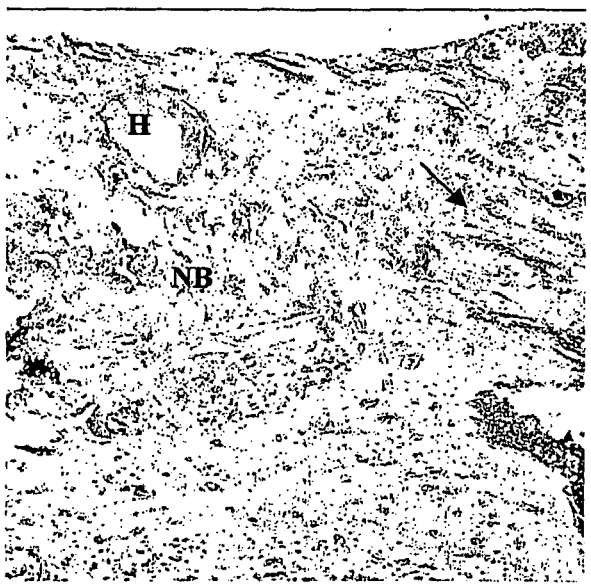

FIGS. 5A and 5B show new bone (NB) formation around the SA-heparin particles (H) four weeks post op. The arrows outline the site of the cut. The entire wedge is filled with new bone. New bone was observed in all the treatments. SA-hep particles are still observed four weeks post op.

4) Table 4 shows the experimental setup designed to test another composition comprising the synthetic apatite-heparin composite. The addition of gelatin to the composite changed its consistency. The composition was injected into holes made in the rat tibiae.

TABLE 4

| No. | Tag | Left leg | Right leg |
|---|---|---|---|
| 1-2 | No tag | SA – HEP + Gelatin | SA – HEP + Gelatin |
| 3-4 | Tail cut | SA – HEP + Gelatin + FGFV | SA – HEP + Gelatin + FGFV |
| 5-6 | Rt ear cut | SA – HEP + Gelatin + FGFV | SA – HEP + Gelatin + FGFV |
| 7-8 | Lt ear cut | Com CaPO4 | Com CaPO4 |
| 9-11 | both ears | Com CaPO4 + Gelatin + FGFV | Com CaPO4 + Gelatin + FGFV |
| 12-13 | No tag | SA – HEP + Gelatin | SA – HEP + Gelatin |
| 14-15 | Tail cut | SA – HEP + Gelatin + FGFV | SA – HEP + Gelatin + FGFV |
| 16-17 | Rt ear cut | SA – HEP + Gelatin + FGFV | SA – HEP + Gelatin + FGFV |

Com $CaPO_4$ = commercially available ceramic calcium phosphate bone substitute

Figure 6A:
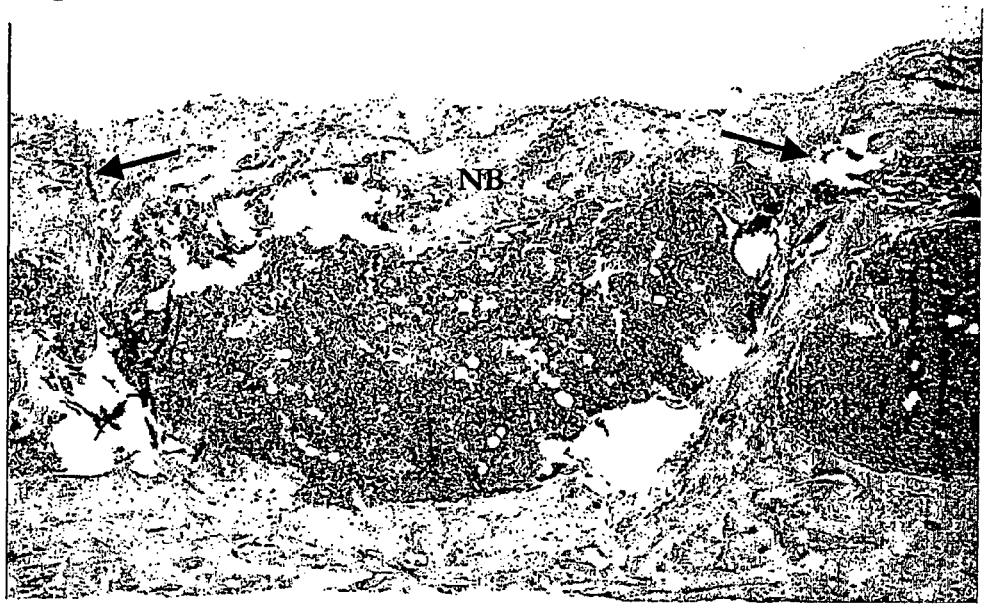
FIGS. 6A through 6D show histological sections of new bone formation in a rat tibia model.
Figure 6B:
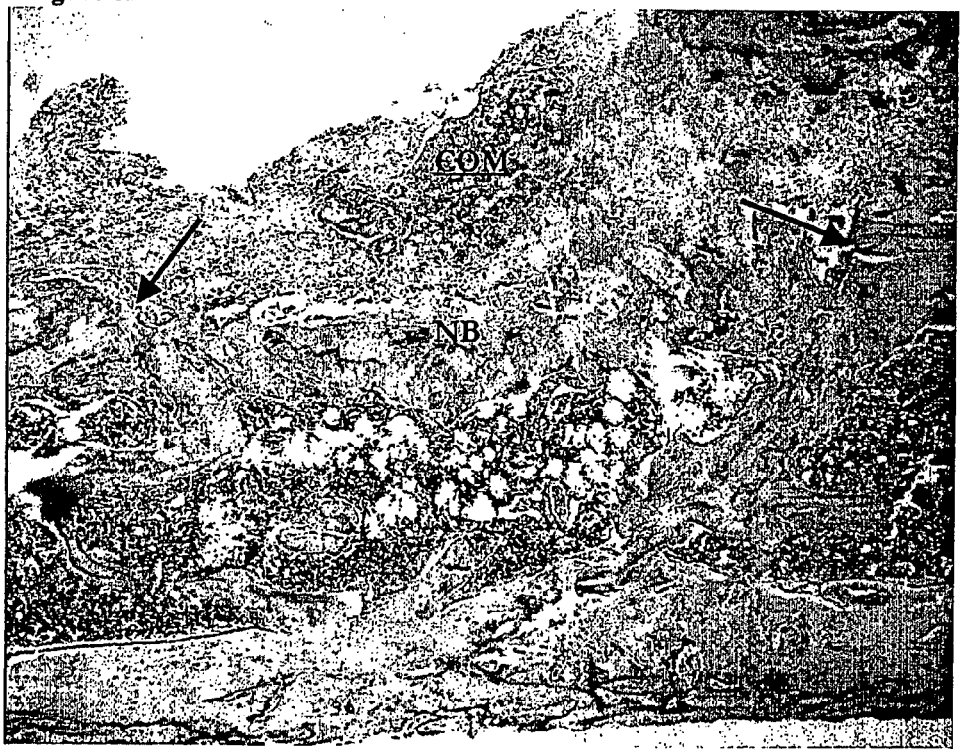
Figure 6C:
Figure 6D:

FIGS. 6A-6D show the healing effect after 4 weeks, using 3 different compositions in the rat tibia model. The arrows demark the extent of the hole. All figures are shown at 40× magnification. NB refers to new bone. FIG. 6A shows new bone formation in an untreated hole, FIG. 6B is new bone surrounding a commercially available calcium phosphate ceramic. FIG. 6C shows the new bone surrounding the SA particles (P) while FIG. 6D shows new bone surrounding SA-hep (P-H) particles. FIG. 6D shows full integration between new bone and SA-hep particles of the present invention.

Example 4 shown in Table 5 was designed to test the effect of a calcium sulfate hardener on administration of the SA composite and its effect on bone repair.

TABLE 5

| No. | Left leg | Right leg |
| --- | --- | --- |
| 1-2 | No treatment | No treatment |
| 3-5 | SA – HEP + CaSO$_4$ | SA – HEP + CaSO$_4$ |
| 6-7 | SA – HEP + CaSO$_4$ + 1 µg FGF | SA – HEP + CaSO$_4$ + 1 µg FGF |
| 8-9 | SA – HEP + CaSO$_4$ + 10 µg FGF | SA – HEP + CaSO$_4$ + 10 µg FGF |

Figure 7A:
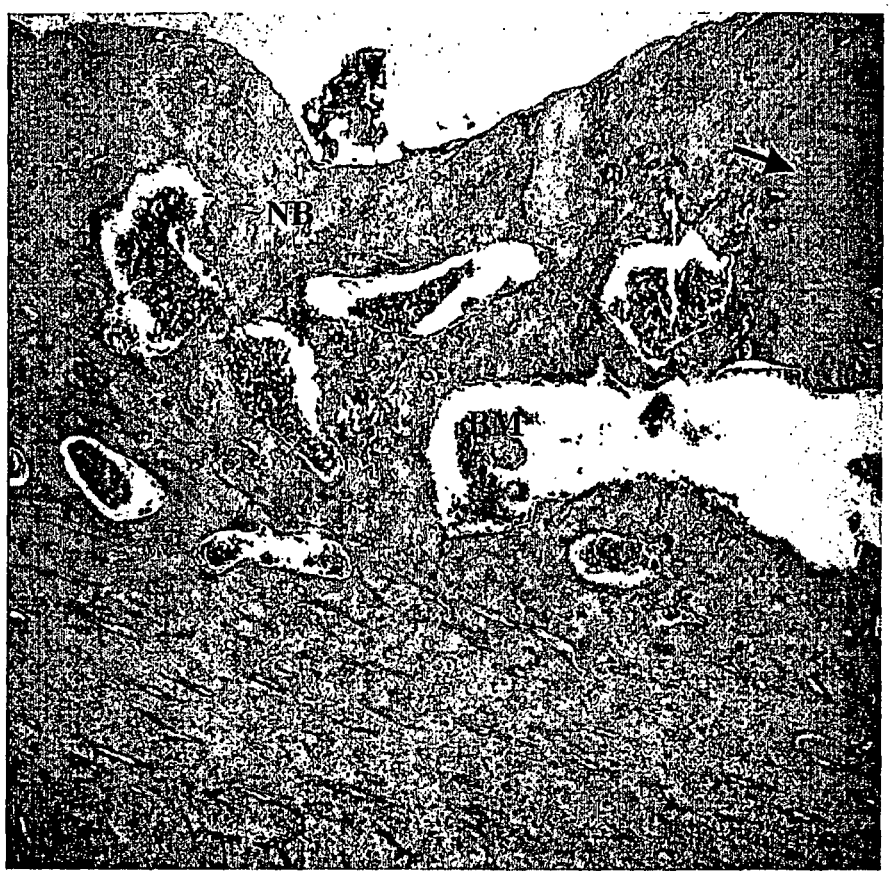
FIGS. 7A and 7B show histological sections of new bone formation in a rat tibia model using a using a synthetic apatite-heparin composite further comprising a calcium sulfate hardening agent.
Figure 7B:

Calcium sulfate was added to the composition to provide in situ hardening of the composition. The calcium sulfate had no detrimental effect on bone formation and all the induced holes filled with new bone within seven weeks. FIG. 7 shows the healing of the filled defects. FIG. 7A shows new bone from a defect filled with an SA-hep calcium sulfate composition. FIG. 7B shows new bone from a defect filled with an SA-hep calcium sulfate composition further comprising FGF.

The experiment was repeated using recombinant BMP2 in place of the FGF, with similar healing results.

Example 11

Rat Calvarial Model

Two rat calvarial defect models are used to determine the efficacy of the composition of the invention to induce bone repair of large defects. In one model, two 3 mm defects per calvaria are drilled using a trephine on both sides of the median suture; one side serves as a control. The protocol and evaluation method is described in Colombier (Colombier et al., Cells Tissues Organs 164:131-140, 1999).

The second model, described in Hollinger (Hollinger and Kleinschmidt, J Craniofacial Surg 1:60-68, 1990) introduces an 8 mm defect in the parietal bone. The defect is filled with the composition of the invention and the incision site sutured. Following 4 weeks the animals are euthanized and the defect sites recovered. Histological analysis proceeds as in example 12.

Example 12

Non-Union Model

Distraction osteogenesis is a useful method for bone elongation of extremities in short stature, for example in individuals diagnosed with different forms of dwarfism such as achondroplasia. This process of bone lengthening is long and often complications arise such as non-union or poor quality of the regenerated bone.

The maximal rate of elongation used in the current procedure of limb elongation, while maintaining proper bone healing and reconstitution is approximately 1 mm/day. Faster elongation rates have resulted in lack of fusion or in the formation of weak bone that breaks easily or is not weight bearing. For this reason, and in order to enable a shorter elongation period with the concomitant formation of strong, healthy bone it is necessary to provide graft substitute that will promote bone regeneration. For optimal comparison to humans, it is important to perform the procedure in a large animal model like sheep, preferably with analogous devices and elongation techniques. The model is adjusted to test enhancing bone formation at an elongation rate of 1.5 mm/day.

Materials and Methods
Treatment arms:
Treatment 1: 6 lambs (6 limbs), Control no treatment
Treatment 2: 6 lambs (6 limbs), fluid bone substitute of the invention
Treatment 3: 6 lambs (6 limbs): Heparin modified synthetic apatite
Treatment 4: 6 lambs (6 limbs): Heparin modified synthetic apatite with FGF2 variant Lambs are assigned randomly into one of the two treatment arms. Surgical lengthening of the right femur is performed in 24 sheep aged from 3 to 4 months.

Anesthesia and pre-mediation: General anesthesia is given without endotracheal intubation. Intramuscular atropine is given as premedication (0.5 mg/kg), and thiopentone sodium-2.5% (10-15 mg/kg), Fentanyl® (0.0015 mg/kg) and Diazepam® (0.2 mg/kg) is administered intravenously.

Fixation: A monolateral external fixator (Monotube-Triax®, Stryker Trauma, Geneva, Switzerland) with four pins, two proximal and two distal in each of its pin clamps, are positioned so that the pins are kept away from the growth plates and the surface of the joint. The osteotomy is performed using a pneumatic saw.

Lengthening: The lengthening procedure begins seven days after surgery for all treatment groups and continues until the limb is lengthened by 5 cm. The total elongation period lasts 33 days, at a rate of 1.5 mm/day.

Treatment 1—Control—To assess the effect during the consolidation period, animals undergo surgery but receive no treatment.

Treatment 2—To assess the effect of the bone substitute, the bone substitute is administered once, one week after completion of elongation.

Treatment 3—To assess the effect of the carrier alone during consolidation period heparin modified synthetic apatite will be administered once, one week after completion of elongation.

Treatment 4—To assess the effect of the product during consolidation period, heparin modified synthetic apatite with FGF2 variant will be administered once, one week after completion of elongation.

Animals are kept in a limited area, during the extent of the whole experiment and will be allowed to feed and walking ad libitum in cage. Animals are weighed at fixed intervals and general well-being is monitored.

To study bone formation in the host bone, four different bone markers fluorochromes are administered IM, according to the following schedule: one week after surgery: calcein (green, Sigma®); two weeks after surgery: alizarin (red, Sigma®); three weeks after surgery: xylenol (orange, Fluka®) and three days before sacrifice oxytetracycline (yellow, Duphacycline®).

Assessment of efficacy: Success is determined by healing and bone quality obtained after elongation.

X-ray: Progress of bone healing will be controlled by X-ray at weeks 1, 2 and 4 after beginning of elongation. The parameters to be assessed from the X-ray are: degree of callus formation, gap closure and remodeling achieved during treatment. X-ray scoring is performed by an orthopedic surgeon, according to established bone healing grading systems.

The Spalteholz technique to analyze the vascularization of the lengthened callus in each group is performed after intraarterial injection of Berlin blue through the femoral artery before sacrifice.

Completion: The animals are sacrificed three months after initial surgery by IV injection of 5 meq of KCl, after anesthesia with sodium pentobarbital (1.5 mg/kg weight).

Histology: The callus is divided into two parts, one for embedding in paraffin, and the other undecalcified for embedding in methylmethacrylate. For the histological study, the specimens are fixed in Bouin for 24 hours and decalcified in a solution of PVP-EDTA, at 4° C. Once specimens are decalcified, they are dehydrated using alcohols of increasing proof (70%, 80%, 96% and 100%), and after 4 hours in xylene, they are embedded in paraffin at a temperature of 60° C. The specimens are sectioned at 4 μm, and stained with Masson's trichrome, hematoxylin and eosin (H&E), safranin-O and von Kossa.

To analyze the mineralization by fluorochromes, the specimens are fixed in formalin for one week, then dehydrated using alcohols of increasing proof. After one week in PMMA-alcohol and three weeks in PMMA (Technovit 7200 VLC®), specimens are sectioned with a diamond saw (Exakt®) and trimmed to a thickness of 14 μm. After measuring the sections with ultraviolet light the distance of the bone markers is measured and the bone index formation calculated (distance mm/days)

The proximal tibiae are extracted and cut in lateral and medial parts. The lateral portion is placed in 4% buffered formaldehyde. After decalcification in EDTA, the specimens are embedded in paraffin and cut into 4 μm slices. The H&E, Masson's trichrome, Safranin-0 and Alcian blue-PAS stains are applied according to standard technique.

Immunohistochemistry: Antibodies to collagen I, collagen II, FGF1, and S-100 are used to detect protein expression in the lengthened callus by an indirect two-step method: 4 μm paraffin sections are trypsinized and deparaffinized. Endogenous peroxidase is blocked by placing the sections in hydrogen peroxidase solution for 30 min. They are incubated in the following reagents with appropriate Tris-buffered-saline (TBS: 0.55 M, pH 7.36) washes: normal pig serum for 30 min, primary antibody for 1 hour, secondary biotinylated antibody for 30 min, and avidin-biotin complex (Dako KO355) for 30 min. The reactions are visualized with chromogen substrate solution (diaminobenzidine, hydrogen peroxidase, TB) and sections are counterstained with Harris's hematoxylin, dehydrated, and mounted. As a negative control, TBS is used instead of the primary antibodies. All stained sections are examined and photographed with use of a microscope (Nikon Optiphot-2®, Japan).

Morphometric analysis: An image analyzing system (Leica Q 500MC®) determines the histomorphometric parameters. The parameters determined using Masson's trichrome stain are: Trabecular width; Trabecular area; Trabecular erosion surface; Index of trabecular erosion; Number of osteoblasts; Number of osteoclasts per field; Number of osteoclast nuclei; Index of bone resorption or number osteoclast nuclei/osteoclasts.

The parameters determined using von Kossa's stain are: Osteoid width; Osteoid-trabecular index; and the fluorescence staining measures the extent of long bone formation.

Example 13

In Vitro and In Vivo Assays for Synthetic Apatite Bisphosphonate Composite

The synthetic apatite-bisphosphonate composite of the present invention was tested for bisphosphonate activity in an in vivo rat model by injecting either SA or a SA-bisphosphonate semi-fluid composition directly into a hole created in the calvarial bone and filling with the composition. The SA-bisphosphonate composite prepared with 1 mg/ml alendronate. The composition was made by mixing equal volumes of the composite with PBS. The animals were sacrificed after 7 days.

Figure 8A:
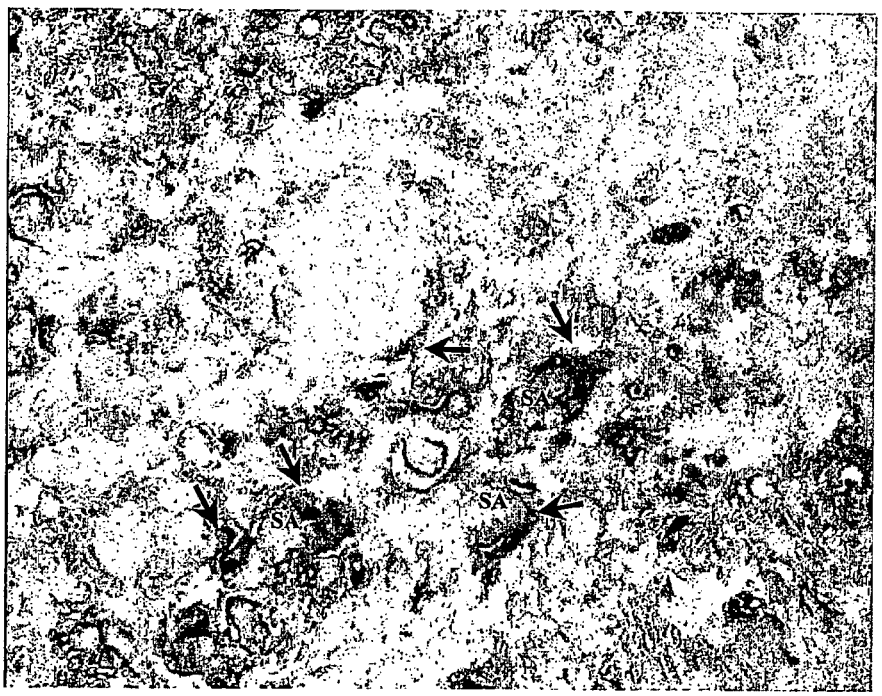
FIGS. 8A and 8B show histological sections of calvarial bone treated with synthetic apatite alone (8A) or synthetic apatite-alendronate composite (8B) stained for osteoclasts using TRAP assay.
Figure 8B:

Histological sections were made and stained for TRAP (Tartrate Resistant Acidic Phosphate), a marker for osteoclasts. TRAP staining is reddish in color. FIG. 8A shows the sections in which SA alone was injected, FIG. 8B shows a section where SA-alendronate was injected. FIG. 8A shows strong TRAP staining on or near many of the SA particles, indicated active bone remodeling around the particles. FIG. 8B shows a section wherein SA-alendronate composition was injected into the calvarial hole. No reddish staining was seen in the vicinity of the particles or within the area of injury strongly suggesting that the anti-resorptive activity of the bisphosphonate is not hindered in the co-precipitation process.

Additional cell assays and animal models include in vitro osteoclast resorption (i.e. Taylor et al., Int J Oral Maxillofac Implants, 17:321-30, 2002), maintenance of alveolar bone following tooth extraction (Denissen, et al, J Periodontol, 71:279-86, 2000), repair of a segmental defect in a canine femur (Fujibayashi et al., J Long Term Eff Med Implants; 11:93-103, 2001), inhibition of debris induced osteolysis caused by prosthesis loosening (Schwarz et al., J Orthop Res, 18:849-55, 2000), a mouse model of inflammatory bone remodeling (JARO 2:65-71, 2001).

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

The invention claimed is:

1. A bone-enhancing composite comprising synthetic apatite and at least one of a biocompatible polymer and an antiresorptive agent added ab initio, wherein the synthetic apatite comprises ionic calcium, phosphate, carbonate and at least one amino acid in monomeric or polymeric form.

2. The bone-enhancing composite according to claim 1 wherein the biocompatible polymer is selected from a natural biocompatible polymer and a synthetic biocompatible polymer, wherein said natural polymer is a polysaccharide.

3. The bone-enhancing composite according to claim 2 wherein said polysaccharide is a glycosaminoglycan.

4. The bone-enhancing composite according to claim 3 wherein said glycosaminoglycan is heparin or a heparin derivative.

5. The bone-enhancing composite according to claim 1 further comprising at least one therapeutic agent.

6. The bone-enhancing composite according to claim 5 wherein the at least one therapeutic agent is selected from the group consisting of antibiotics, antiviral agents, chemotherapeutic agents, anti-rejection agents, analgesics, anti-inflammatory agents, hormones, growth factors and cytokines.

7. The bone-enhancing composite according to claim 6 wherein said at least one therapeutic agent is a growth factor.

8. The bone-enhancing composite according to claim 7 wherein said growth factor is a fibroblast growth factor or an active fragment or variant thereof.

9. The bone-enhancing composite according to claim 1 wherein said synthetic apatite is a poorly crystalline apatite.

10. The bone-enhancing composite according to claim 1 wherein said synthetic apatite is a poorly crystalline apatite and said biocompatible polymer is heparin or a heparin derivative.

11. The bone-enhancing composite according to claim 10 further comprising fibroblast growth factor or an active fragment or variant thereof.

12. The bone-enhancing composite according to claim 1 wherein the anti-resorptive agent is a bisphosphonate or a pharmaceutically acceptable salt or ester thereof.

13. The bone-enhancing composite according to claim 9 wherein said poorly crystalline apatite having an X-ray diffraction pattern comprising a peak at a 2 theta value of about 26° and an undifferentiated peak at 2 theta values of about 31° to about 33°.

14. A method for treating orthopedic, periodontal and craniofacial indications comprising administering to a subject in need thereof a therapeutically effective amount of a composition comprising synthetic apatite and at least one of a biocompatible polymer and an anti-resorptive agent added ab initio, wherein the synthetic apatite comprises ionic calcium, phosphate, carbonate and at least one amino acid in monomeric or polymeric form.

15. The method according to claim 14 wherein said biocompatible polymer is a glycosaminoglycan.

16. The method according to claim 15 wherein said glycosaminoglycan is heparin or a heparin derivative.

17. The method according to claim 14 further comprising at least one therapeutic agent.

18. The method according to claim 17 wherein the at least one therapeutic agent is selected from the group consisting of antibiotics, antiviral agents, chemotherapeutic agents, anti-rejection agents, analgesics, anti-inflammatory agents, hormones, growth factors and cytokines.

19. The method according to claim 18 wherein said at least one therapeutic agent is a growth factor.

20. The method according to claim 19 wherein said growth factor is a fibroblast growth factor or an active fragment or variant thereof.

21. The method according to claim 14 wherein said synthetic apatite is a poorly crystalline apatite and said biocompatible polymer is heparin or a heparin derivative.

22. The method according to claim 21 further comprising fibroblast growth factor or an active fragment or variant thereof.

23. The method according to claim 14 wherein the anti-resorptive agent is a bisphosphonate or a pharmaceutically acceptable salt or ester thereof.

24. A method of preparing a bone enhancing composite comprising synthetic apatite and at least one of a biocompatible polymer and an anti-resorptive agent added ab initio, wherein the synthetic apatite comprises ionic calcium, phosphate, carbonate and at least one amino acid in monomeric or polymeric form, the method comprising the steps of:
   a) preparing a liquid mixture comprising ionic calcium, phosphate, at least one amino acid in either monomeric or polymeric form, carbonate, at least one of a biocompatible polymer and an anti-resorptive agent, optionally further comprising a therapeutic agent;
   b) subjecting said mixture to microwave irradiation;
   c) quenching said irradiated mixture;
   d) filtering said quenched mixture so as to separate between the filtrate and a cake;
   e) drying said cake;
   f) grinding said cake into a powder.

25. The method according to claim 24 further comprising the following steps:
   g) sterilizing said powder;
   h) wetting said sterilized powder with a solution optionally comprising at least one therapeutic agent;
   i) preparing said wetted powder for administration.

26. The method according to claim 24 wherein the biocompatible polymer is heparin or a heparin derivative.

27. The method according to claim 24 further comprising at least one therapeutic agent.

28. The method according to claim 27 wherein the at least one therapeutic agent is selected from the group consisting of antibiotics, antiviral agents, chemotherapeutic agents, anti-rejection agents, analgesics, anti-inflammatory agents, hormones, growth factors and cytokines.

29. The method according to claim 28 wherein said at least one therapeutic agent is a growth factor.

30. The method according to claim 29 wherein said growth factor is a fibroblast growth factor or an active fragment or variant thereof.

31. The method according to claim 24 wherein the anti-resorptive agent is a bisphosphonate or a pharmaceutically acceptable salt or ester thereof.

32. The method according to claim 24 wherein said synthetic apatite is a poorly crystalline apatite having an X-ray diffraction pattern comprising a peak at a 2 theta value of about 26° and an undifferentiated peak at 2 theta values of about 31° to about 33°.

* * * * *

UNITED STATES PATENT AND TRADEMARK OFFICE
CERTIFICATE OF CORRECTION

| | | |
|---|---|---|
| PATENT NO. | : 7,887,831 B2 | Page 1 of 1 |
| APPLICATION NO. | : 10/534794 | |
| DATED | : February 15, 2011 | |
| INVENTOR(S) | : Avner Yayon | |

It is certified that error appears in the above-identified patent and that said Letters Patent is hereby corrected as shown below:

Title Page
In the Assignee Item (73): Delete "Hepacore Ltd., Ness Ziona (IL)" and insert --Prochron Biotech Ltd., Ness Ziona (IL)--

Signed and Sealed this
Twenty-sixth Day of July, 2011

David J. Kappos
*Director of the United States Patent and Trademark Office*